US012691199B2

(12) United States Patent
Alrashoudi et al.

(10) Patent No.: US 12,691,199 B2
(45) Date of Patent: Jul. 28, 2026

(54) MUSSEL-INSPIRED PHOTOREACTIVE INSTANT GLUE FOR ENVIRONMENTAL AND BIOMEDICAL APPLICATIONS

(71) Applicant: KING ABDULLAH UNIVERSITY OF SCIENCE AND TECHNOLOGY, Thuwal (SA)

(72) Inventors: Abdulelah A. Alrashoudi, Thuwal (SA); Panagiotis Bilalis, Thuwal (SA); Charlotte A.E. Hauser, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 18/873,438

(22) PCT Filed: Jun. 19, 2023

(86) PCT No.: PCT/IB2023/056328
§ 371 (c)(1),
(2) Date: Dec. 10, 2024

(87) PCT Pub. No.: WO2023/248105
PCT Pub. Date: Dec. 28, 2023

(65) Prior Publication Data

US 2025/0170298 A1 May 29, 2025

Related U.S. Application Data

(60) Provisional application No. 63/353,927, filed on Jun. 21, 2022.

(51) Int. Cl.
*A61L 24/04* (2006.01)
*A61L 24/10* (2006.01)
*C08F 220/60* (2006.01)

(52) U.S. Cl.
CPC ............. *A61L 24/046* (2013.01); *A61L 24/10* (2013.01); *C08F 220/603* (2020.02); *C08F 2800/10* (2013.01); *C08F 2810/20* (2013.01)

(58) Field of Classification Search
CPC ....... C08L 23/0869; C08L 33/08; C07K 1/02; C07K 1/10; C07K 5/06086; C07K 7/02
See application file for complete search history.

(56) References Cited

U.S. PATENT DOCUMENTS

| | | | |
|---|---|---|---|
| 5,445,612 A | 8/1995 | Terakura et al. | |
| 5,543,034 A | 8/1996 | Hilbertz et al. | |
| 2003/0175410 A1 | 9/2003 | Campbell et al. | |
| 2007/0154552 A1 | 7/2007 | Siegal et al. | |
| 2008/0095748 A1 | 4/2008 | Kharazi et al. | |
| 2011/0008293 A1 | 1/2011 | Bhandari | |
| 2011/0287067 A1* | 11/2011 | Stewart .................. | A61L 24/06 514/8.8 |
| 2014/0012225 A1 | 1/2014 | Yoo et al. | |
| 2015/0038428 A1 | 2/2015 | Hauser et al. | |
| 2016/0288414 A1 | 10/2016 | Ozbolat et al. | |
| 2017/0056548 A1 | 3/2017 | Lee et al. | |
| 2018/0118978 A1 | 5/2018 | Yabu et al. | |
| 2019/0364854 A1 | 12/2019 | Woldman | |
| 2020/0148720 A1 | 5/2020 | Hauser et al. | |
| 2020/0199514 A1 | 6/2020 | Hauser et al. | |
| 2022/0054706 A1 | 2/2022 | Hauser et al. | |
| 2022/0322644 A1 | 10/2022 | Chen et al. | |
| 2022/0371958 A1 | 11/2022 | Hauser et al. | |
| 2023/0295225 A1 | 9/2023 | Hauser et al. | |

(Continued)

FOREIGN PATENT DOCUMENTS

| | | |
|---|---|---|
| CN | 105 881 908 A | 8/2016 |
| JP | 2013 009598 A | 1/2013 |
| KR | 2016 0091993 A | 8/2016 |

(Continued)

OTHER PUBLICATIONS

Xiong, Xiong, Oxidation Communications 40, No. 1-1, pp. 248-255 (2017) (Year: 2017).*
Li, Yiran, Nature Communications (2020)11: 3895 (Year: 2020).*
Zhang et al., "Catechol funcationalized hyperbranched polymers as biomedical materials", Science Direct, vol. 76, pp. 47-55 (2018).
Written Opinion of the International Searching Authority received in PCT Application No. PCT/IB2023/056238 dated Oct. 13, 2023.
International Search Report received in PCT Application No. PCT/IB2023/056238 dated Oct. 13, 2023.
Waite, J. H., "The Formation of Mussel Byssus: Anatomy of a Natural Manufacturing Process," Structure, Cellular Synthesis and Assembly of Biopolymers, 27-54 (1992).
Coyne, K. J., et al. "Extensible Collagen in Mussel Byssus: A Natural Block Copolymer," Science 277, 1830-1832 (1997).

(Continued)

*Primary Examiner* — Brian-Yong S Kwon
*Assistant Examiner* — Lyndsey M Beckhardt
(74) *Attorney, Agent, or Firm* — Ajay A. Jagtiani; Miles & Stockbridge P.C.

(57) ABSTRACT

Nature-inspired smart materials offer numerous advantages over environment-friendliness and efficiency. Emulating the excellent adhesive properties of mussels foot proteins, where the Lysine is in close proximity with the 3, 4-dihydroxy-L-phenylalanine (DOPA), embodiments report the synthesis of a novel photo-curable peptide-based adhesive consisting exclusively of these two amino acids. The adhesive is a highly concentrated aqueous solution of a monomer, a crosslinker and a photoinitiator. No toxicity of the adhesive was observed when the cytocompatibility on human dermal fibroblast cells was assessed. Lap-shear adhesion measurements on plastic and glass surfaces and comparison with different types of commercial adhesives showed that the adhesive strength of the disclosed glue is comparable when applied in the air and superior when used underwater. Given the convenience of the facile synthesis, biocompatibility, ease of application underwater and high adhesive strength, embodiments expect that the adhesive may find application, but not limited, to the biomedical field.

5 Claims, 27 Drawing Sheets

(56) References Cited

U.S. PATENT DOCUMENTS

| | | | |
|---|---|---|---|
| 2023/0405177 | A1 | 12/2023 | Hauser et al. |

FOREIGN PATENT DOCUMENTS

| | | | |
|---|---|---|---|
| KR | 20190128405 | A | 11/2019 |
| KR | 10-2020-0007537 | A | 1/2020 |
| KR | 10-2021-0104339 | A | 8/2021 |
| WO | 2005/014615 | A2 | 2/2005 |
| WO | 2007/102735 | A1 | 9/2007 |
| WO | 2008/057608 | A2 | 5/2008 |
| WO | 2012/048755 | A1 | 4/2012 |
| WO | 2013/126017 | A1 | 8/2013 |
| WO | 2014/104981 | A1 | 7/2014 |
| WO | 2014/197999 | A1 | 12/2014 |
| WO | 2015/066705 | A1 | 5/2015 |
| WO | 2015/080670 | A1 | 6/2015 |
| WO | 2015/080671 | A1 | 6/2015 |
| WO | 2016/144259 | A1 | 9/2016 |
| WO | 2016/181408 | A1 | 11/2016 |
| WO | 2018/207036 | A1 | 11/2018 |
| WO | 2018/207037 | A1 | 11/2018 |
| WO | 2020/162835 | A1 | 8/2020 |
| WO | 2021/070083 | A1 | 4/2021 |

OTHER PUBLICATIONS

Cui, C., et al. "Recent advances in wet adhesives: Adhesion mechanism, design principle and applications." Prog. Polym. Sci. 116, 101388 (2021).

Strausberg R. L., et al. "Protein-based medical adhesives." Trends in biotechnology 8, 53-57 (1990).

Rosano, G.L., et al. "Recombinant protein expression in *Escherichia coli*: advances and challenges." Front. Microbiol. 5, 172 (2014).

Silverman, H. G., et al. "Understanding Marine Mussel Adhesion." Mar. Biotechnol. 9, 2661-681 (2007).

Forooshani P. K., et al. "Recent Approaches in Designing Bioadhesive Materials Inspired by Mussel Adhesive Protein." J. Polym. Sci., Part A: Polym. Chem. 55, 9-33 (2017).

Li, Y., et al. "Single Molecule Evidence for the Adaptive Binding of DOPA to Different Wet Surfaces." Langmuir 30, 4358-4366 (2014).

Shin, J., et al. "Tissue Adhesive Catechol-Modified Hyaluronic Acid Hydrogel for Effective, Minimally Invasive Cell Therapy." Adv. Funct. Mater. 25, 3814-3824 (2015).

Yan, S., et al. "Preparation of mussel-inspired injectable hydrogels based on dual-functionalized alginate with improved adhesive, self-healing, and mechanical properties." J. Mater. Chem. B. 6, 6377-6390 (2018).

Ju, Y., et al. "Engineered Metal-Phenolic Capsules Show Tunable Targeted Delivery to Cancer Cells." Biomacromolecules 17, 2268-2276 (2012).

Kim, K., et al. "Bio-inspired catechol conjugation converts water-insoluble chitosan into a highly water-soluble, adhesive chitosan derivative for hydrogels and LbL assembly." Biomater. Sci. 1, 783-790 (2013).

Neto, A. I., et al. "Nanostructured Polymeric Coatings Based on Chitosan and Dopamine-Modified Hyaluronic Acid for Biomedical Applications." Small 10, 2459-2469 (2014).

Zhou, D., et al. "Dopamine-Modified Hyaluronic Acid Hydrogel Adhesives with Fast-Forming and High Tissue Adhesion." ACS Appl. Mater. Interfaces 12, 18225-18234 (2020).

Zhu, W., et al. "A novel DOPA-albumin-based tissue adhesive for internal medical applications." Biomaterials 147, 99-115 (2017).

Gowda, AHJ., et al. "Design of tunable gelatin-dopamine based bioadhesives." Int. J. Biol. Macromol. 164, 1384-1391 (2020).

Di, X., et al. "Bioinspired tough, conductive hydrogels with thermally reversible adhesiveness based on nanoclay confined NIPAM polymerization and a dopamine modified polypeptide." Mater. Chem. Front. 4, 189-196 (2020).

Tatehata, H., et al. "Model polypeptide of mussel adhesive protein. I. Synthesis and adhesive studies of sequential polypeptides (X-Tyr-Lys)n and (Y-Lys)n." Journal of Applied Polymer Science 76, 929-937 (2000).

Ahn, B. K., et al. "High-performance mussel-inspired adhesives of reduced complexity." Nat. Commun. 6, 8663-8669 (2015).

North, M. A., et al. "High Strength Underwater Bonding with Polymer Mimics of Mussel Adhesive Proteins." ACS Appl. Mater. Interfaces 9, 7866-7872 (2017).

Zhao, Q., et al. "Underwater contact adhesion and microarchitecture in polyelectrolyte complexes actuated by solvent exchange." Nat. Mater. 15, 407-412 (2016).

Burke, S. A., et al. "Thermal gelation and tissue adhesion of biomimetic hydrogels." Biomedical Materials 2, 203-210 (2007).

Montazerian, H., et al. "Stretchable and Bioadhesive Gelatin Methacryloyl-Based Hydrogels Enabled by in Situ Dopamine Polymerization." ACS Appl. Mater. Interfaces 13, 40290-40301 (2021).

Skelton, S., et al. "Biomimetic adhesive containing nanocomposite hydrogel with enhanced materials properties." Soft Matter 9, 3825-3833 (2013).

Patil, N., et al. "Mussel-inspired protein-repelling ambivalent block copolymers: controlled synthesis and characterization." Polym. Chem. 6, 2919-2933 (2015).

Wilker, J. J., "Positive charges and underwater adhesion." Science 349, 582-583 (2015).

Maier, G. P., et al. "Adaptive synergy between catechol and Lysine promotes wet adhesion by surface salt displacement." Science 349, 628-632 (2015).

Statz, A. R., et al. "New Peptidomimetic Polymers for Antifouling Surfaces." J. Am. Chem. Soc. 127, 7972-7973 (2005).

Shin, M., et al. "The position of Lysine controls the catechol-mediated surface adhesion and cohesion in underwater mussel adhesion." J. Colloid Interface Sci. 563, 168-176 (2020).

Zhang, C., et al. "Tough and alkaline-resistant mussel-inspired wet adhesion with surface salt displacement via polydopamine/amine synergy." Langmuir 35, 5257-5263 (2019).

Zhang, J., et al. "Quantifying cation—• interactions in marine adhesive proteins using single-molecule force spectroscopy." Supramolecular Materials 1, 100005 (2022).

Geng, H., et al. "Principles of Cation-TT Interactions for Engineering Mussel-Inspired Functional Materials." Acc. Chem. Res. 55, 1171-1182 (2022).

Tiu, B.D.B., et al. "Cooperativity of Catechols and Amines in High-Performance Dry/Wet Adhesives." Angewandte Chemie 132, 16759-16767 (2020).

Rapp, M. V., et al. Defining the Catechol-Cation Synergy for Enhanced Wet Adhesion to Mineral Surfaces. J. Am. Chem. Soc. 138, 9013-9016 (2016).

Thumwanit, V., et al. "Cytotoxicity of polymerized commercial cyanoacrylate adhesive on cultured human oral fibroblasts." Aust. Dent. J. 44, 248-252 (1999).

Leggat, P. A., et al. "Surgical applications of cyanoacrylate adhesives: a review of toxicity." Anz J. Surg. 77, 209-213 (2007).

Forsman, Z. H., et al. "Growing coral larger and faster: micro-colony-fusion as a strategy for accelerating coral cover." PeerJ. 3, e1313 (2015).

Albalawi, H. I., et al. "Sustainable and Eco-Friendly Coral Restoration through 3D Printing and Fabrication." ACS Sustainable Chem. Eng. 9, 12634-12645 (2021).

Alshehri, S., et al. Scaffolds from Self-Assembling Tetrapeptides Support 3D Spreading, Osteogenic Differentiation, and Angiogenesis of Mesenchymal Stem Cells. Biomacromolecules 22, 2094-2106 (2021).

Greaves, S. J., et al. "Vibrational spectra of catechol, catechol-d2 and -d6 and the catecholate monoanion." Spectrochim. Acta Part A Mol. Spectrosc. 47, 133-140 (1991).

Maiti, N. C., et al. "Raman Spectroscopic Characterization of Secondary Structure in Natively Unfolded Proteins: a- Synuclein." J. Am. Chem. Soc. 126, 2399-2408 (2004).

Lima Jr, J. A., et al. "Raman scattering of L-valine crystals." J. Raman Spectrosc. 36, 1076-1081 (2005).

Nyquist, R. A., "Interpreting Infrared, Raman, and Nuclear Magnetic Resonance Spectra." Academic Press 231-350 (2001).

(56) References Cited

OTHER PUBLICATIONS

Lee, J. Y., et al. "Raman intensities of C=C stretching vibrational frequencies of polyenes: Nodal mode analysis." J. Chem. Phys. 107, 4112-4117 (1997).
MacBeath, R., et al. "Cell shape, cytoskeletal tension, and RhoA regulate stem cell lineage commitment." Dev. Cell. 6, 483-495 (2004).
Katz, B. Z., et al. "Physical state of the extracellular matrix regulates the structure and molecular composition of cell- matrix adhesions." Mol. Biol. Cell. 11, 1047-1060 (2000).
Shin, M., et al. "Two faces of amine-catechol pair synergy in underwater cation— π interactions." Chemistry of Materials 33, 3196-3206 (2021).
Lim, C., et al. "Nanomechanics of poly (catecholamine) coatings in aqueous solutions." Angewandte Chemie International Edition 55, 3342-3346 (2016).
Miclotte, M. P. J., et al. "Thermoresponsive Block Copolymer Core-Shell Nanoparticles with Tunable Flow Behavior in Porous Media." ACS Appl. Mater. Interfaces 14, 54182-5419 (2022).
Extended European Search Report received in European Application No. 21857887.0 dated Sep. 23, 2024.
Arab et al., "Evaluation of peptide nanogels for accelerated wound healing in normal micropigs", Frontiers in Nanoscience and Nanotechnology, vol. 4, pp. 1-9 (2018).
Arab, "Novel Nanofibrous Peptide Scaffolds for Tissue Regeneration", PhD Thesis, XP055901075 (2019).
Ceylan et al., "Mussel Inspired Dynamic Cross-Linking of Self-Healing Peptide Nanofiber Network", Advanced Functional Materials, vol. 23, pp. 2081-2090 (2013).
Chakraborty et al., "A Self-Healing, All-Organic, Conducting, Composite Peptide Hydrogel as Pressure Sensor and Electrogenic Cell Soft Substrate", ACS Nano, vol. 13, pp. 163-175 (2019).
Cringoli et al., "Bioadhesive supramolecular hydrogel from unprotected short D,L-peptides with Phe-Phe and Leu-Asp-Val motifs", Royal Society of Chemistry, vol. 56, pp. 3015-2018 (2020).
Dooley et al., "Selective Ligands for the u, S, and x Opiod Receptors Identified from a Single Mixture Based Tetrapeptide Positional Scanning Combinatorial Library", The Journal of Biological Chemistry, vol. 278, No. 30, pp. 18848-18856 (1998).
Duncan et al., "Short Peptides in Minimalistic Biocatalyst Design", Biocatalysis, No. 1, pp. 67-81 (2015).
Extended European Search Report received in European Application No. 21863813.8 dated Sep. 9, 2024.
Extended European Search Report received in European Application No. 21857886.2 dated Jul. 29, 2024.
Extended European Search Report received in European Application No. 21882283.1 dated Sep. 16, 2024.
Feng et al., "Development of a Potent Thrombin Receptor Ligand", J. Med. Chem., vol. 38, pp. 4125-4130 (1995).
Final Office Action received in U.S. Appl. No. 17/401,434 dated Jul. 17, 2024.
Lee et al., "Enzyme-crosslinked gene-activated matrix for the induction of mesenchymal stem cells in osteochondral tissue regeneration", Acta Biomaterialia, vol. 63, pp. 210-226 (2017).
Li et al., "Peptide-Templated Synthesis of TiO2, Nanofibers with Tunable Photocatalytic Activity", Chem. Eur. J., vol. 24, pp. 18123-18129 (2018).
Liu et al., "Stiffness-mediated mesenchymal stem cell fate decision in 3D-bioprinted hydrogels", Burns & Trauma, vol. 8, tkaa029 (2020).
Nakatsu et al., "An Optimized Three-Dimensional In Vitro Model for the Analysis of Angiogenesis", Methods in Enzymology, vol. 443, pp. 65-82 (2008).
Ramirez-Calderon et al., "Delivery of Endothelial Cell-Laden Microgel Elicits Angiogenesis in Self-Assembling Ultrashort Peptide Hydrogels in Vitro", ACS Appl. Mater. Interfaces, vol. 13, pp. 29281-29292 (2021).
Restu et al., "Short Oligopeptides for Biocompatible and Biodegradeable Supremolecular Hydrogels", Langmuir, vol. 34, pp. 8065-8074 (2018).
Notification of the Substantive Examination Report received in Saudi Arabian Application No. 523440449 dated Aug. 27, 2024.
Shin et al., "The position of lysine controls the catechol-mediated surface adhesion and cohesion in underwater mussel adhesion", Journal of Colloid and Interface science, vol. 563, pp. 168-176 (2020).
Thota et al. "Molecular insights into the self-assembly of short amphiphilic peptides FmDn and FmKn", RSC Adv., vol. 4, pp. 60/41-60/48 (2014).
Written Opinion received in Singaporean Application No. 10202112428Y dated Sep. 18, 2024.
Zhang et al., "Compatability of Neural Stem Cells with Functionalized Self-assembling Peptide Scaffold In vitro", Biotechnology and Bioprocess Engineering, vol. 15, pp. 545-551 (2010).
Zhang et al., "Catechol functionalized hyperbranched polymers as biomedical materials", Polymers in Polymer Science, vol. 78, pp. 47-55 (2018).
Examination Report received in Saudi Arabian Application No. 523442624 mailed Sep. 28, 2023.
Written Opinion received in Singapore Application No. 10202112455P dated Jul. 11, 2023.
Office Action received in Japanese Application No. 2019-561848 dated May 22, 2023.
Notice of Final Rejection received in Korean Application No. 10-2019-7036272 dated May 25, 2023.
European Search Report received in European Application No. 23159765.9 dated Jun. 22, 2023.
Ali et al., "A Non-Canonical NRPS Is Involved in the Synthesis of Fungisporin and Related Hydrophobic Cyclic Tetrapeptides in Penicillium chrysogenum", PLOS One; vol. 9, Issue 6, e98212 (2014).
Pubchem CID: 93078 "L-Aspartyl-L_phenylalanine" (2005).
Vasco et al., "Macrocyclization of Peptide Side Chains by the Ugi Reaction: Achieving Peptide Folding and Exocyclic N-Functionalization in One Shot", The Journal of Organic Chemistry, 80, pp. 6697-6707 (2015).
Written Opinion received in Singapore Application No. 1020112455P dated Mar. 27, 2024.
Examination Report received in Saudi Arabian Application No. 523442596 dated Mar. 31, 2024.
Non-Final Office Action received in U.S. Appl. No. 18/021,645 dated Apr. 1, 2024.
Office Action received in U.S. Appl. No. 17/401,434 dated Jan. 24, 2025.
Office Action received in U.S. Appl. No. 17/401,434 dated Jun. 11, 2025.
Examination Report received in Saudi Arabian Application No. 523442596 dated Feb. 24, 2026.
Examination Report received in Saudi Arabian Application No. 523451783 dated Nov. 26, 2024.
Restriction Requirement received in U.S. Appl. No. 18/873,438 dated Mar. 28, 2025.
Office Action received in U.S. Appl. No. 18/210,684 dated Feb. 27, 2025.
Chen et al., "Hydrogelation of the Short Self-Assembling Peptide 13QGK Regulated by Transglutaminase and Use for Rapid Hemostasis", Applied Materials & Interfaces, vol. 8, pp. 17833-17841 (2016).
Rauf et al., "Self-assembling tetrameric peptides allow in situ 3D printing under physiological conditions", J. Mater. Chem. B, vol. 9, pp. 1069-1081 (2021).
Office Action received in U.S. Appl. No. 18/021,596 dated Mar. 4, 2026.
Tao et al., "Fmoc-Modified Amino Acids and Short Peptides: Simple Bio-Inspired Building Blocks for the Fabrication of Functional Materials", Chemical Society Reviews, pp. 1-3 (2012).

* cited by examiner

MUSSEL-INSPIRED PHOTOREACTIVE INSTANT GLUE FOR ENVIRONMENTAL AND BIOMEDICAL APPLICATIONS

BACKGROUND

Field of the Invention

The present disclosure relates to generally to a mussel-inspired photoreactive instant glue for environmental and biomedical applications.

Background of the Invention

Organisms, such as barnacles and mussels have evolved to produce and secrete materials that adhere under harsh conditions. Despite its excellent properties, extracting this adhesive substance requires approximately 10,000 mussels to obtain only one gram of product. Consequently, a need exists for developing a cost-effective adhesive material that can offer enormous applications in medicine, biomedical engineering, nanotechnology, and many others technologies.

SUMMARY

According to first broad aspect, the present disclosure provides a compound comprising a structure of Formula 1, a is from 1 to 6, R is at least one selected from the group consisting of hydrogen, —O—$(CH_2)_b$, and $(CH_2)_b$, b is from 1 to 6, and n is 3 to 8 times higher than m.

Formula 1

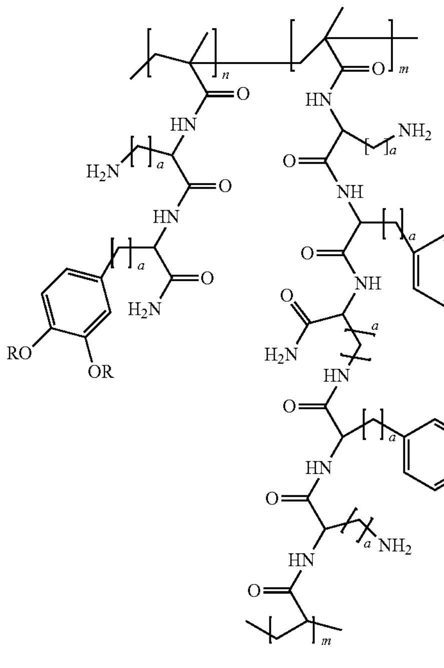

According to a second broad aspect, the present disclosure provides a compound comprising a structure of Formula 2, n is 3 to 8 times higher than m.

Formula 2

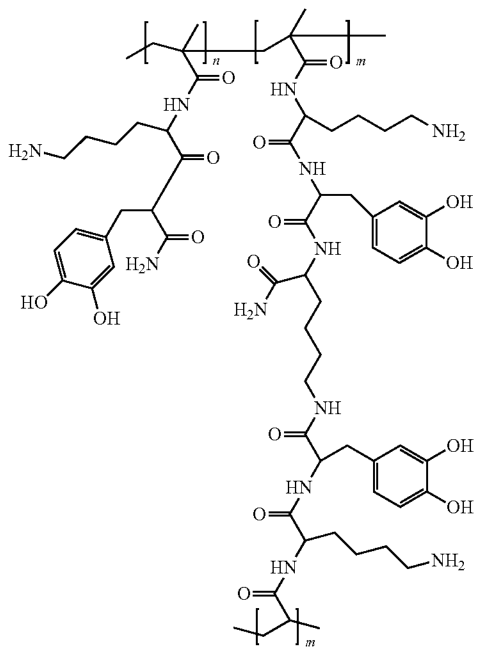

According to a third broad aspect, the present disclosure provides a method of manufacturing a peptide-based adhesive material comprises mixing an aqueous solution of a catechol-based monomer, a catechol-based crosslinker, and a photoinitiator to form a first solution, applying the first solution to a first substrate to form a second substrate, attaching a third substrate to the second substrate to form a fourth substrate, and exposing the fourth substrate to light to attach the first and the third substrate.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

Definitions

Figure 1:
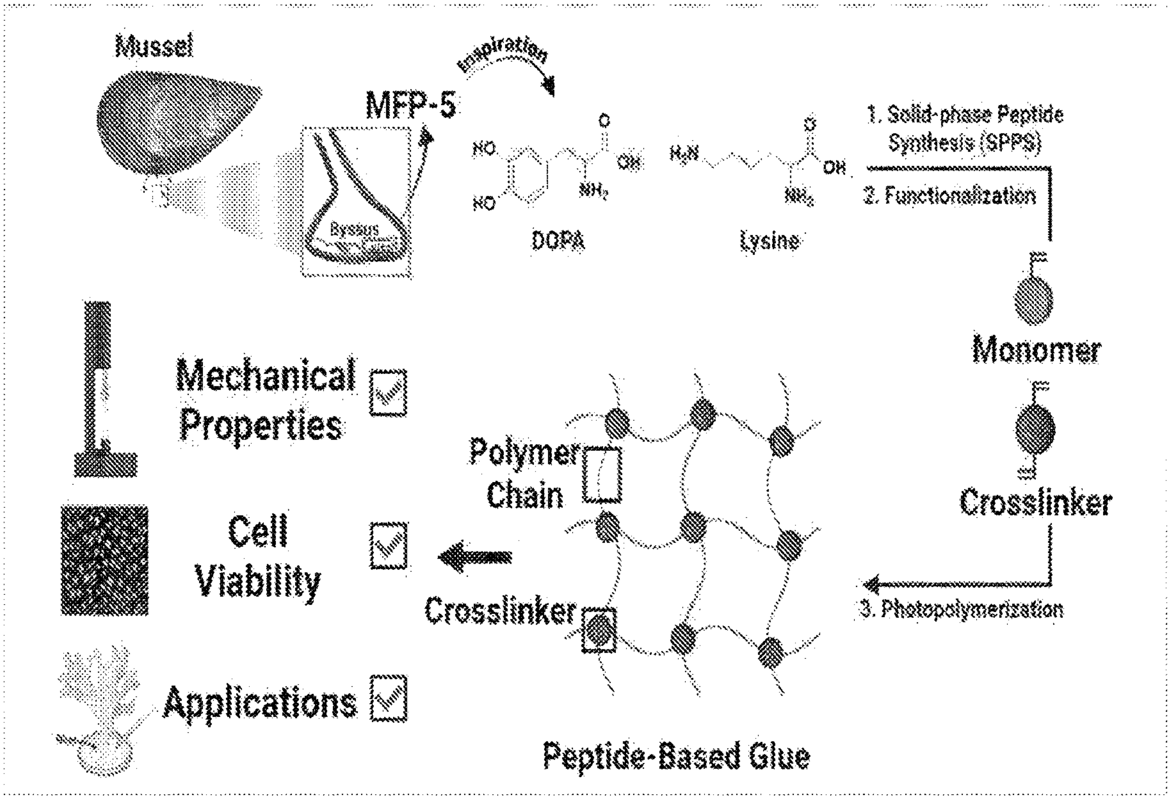
FIG. 1 illustrates synthesis of a strong, non-toxic, photocurable peptide-based adhesive consisting exclusively of DOPA and Lysine with high performance in underwater adhesion for environmental and biomedical applications according to one embodiment of the present disclosure.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

The section headings used herein are for organizational purposes only and are not to be construed as limiting the subject matter described.

Definition of standard chemistry terms may be found in reference works, including but not limited to, Carey and Sundberg "ADVANCED ORGANIC CHEMISTRY 4TH ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/of" unless stated otherwise. Furthermore, use of the term "including" as well as other forms, such as "include", "includes," and "included," is not limiting.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, "a value" or "property" is "based" on a particular value, property, the satisfaction of a condition, or other factor, if that value is derived by performing a mathematical calculation or logical decision using that value, property or other factor.

For purposes of the present disclosure, the term "comprising", the term "having", the term "including," and variations of these words are intended to be open-ended and mean that there may be additional elements other than the listed elements.

For purposes of the present disclosure, the term "analogue" and the term "analog" refer to one of a group of chemical compounds that share structural and/or functional similarities but are different in respect to elemental composition. A structural analog is a compound having a structure similar to that of another one, but differing from it in respect of one or more components, such as one or more atoms, functional groups, or substructures, etc. Functional analogs are compounds that has similar physical, chemical, biochemical, or pharmacological properties. Functional analogs are not necessarily also structural analogs with a similar chemical structure.

For purposes of the present disclosure, the term "amino acid" refers to the molecules composed of terminal amine and carboxylic acid functional groups with a carbon atom between the terminal amine and carboxylic acid functional groups sometimes containing a side chain functional group attached to the carbon atom (e.g. a methoxy functional group, which forms the amino acid serine). Typically, amino acids are classified as natural and non-natural. Examples of natural amino acids include glycine, alanine, valine, leucine, isoleucine, proline, phenylananine, tyrosine, tryptophan, serine, threonine, cysteine, methionine, asparagine, glutamine, lysine, arginine, histidine, aspartate, and glutamate, among others. Examples of non-natural amino acids include L-3, 4-dihydroxyphenylalanine, 2-aminobutyric acid, dehydralanine, g-carboxyglutamic acid, carnitine, gamma-aminobutyric acid, hydroxyproline, and selenomethionine, among others. In the context of this specification it should be appreciated that the amino acids may be the L-optical isomer or the D-optical isomer.

For purposes of the present disclosure, the term "eco-friendly" refers to no toxicity and biodegradable.

For purposes of the present disclosure, the term "effective amount" refers to an amount of an agent sufficient to produce one or more desired effects. The effective amount may be determined by a person skilled in the art using the guidance provided herein.

For purposes of the present disclosure, the term "enhance" and the term "enhancing" refer to increasing or prolonging either in potency or duration of a desired effect.

For purposes of the present disclosure, the term "light" refers to any type of electromagnetic radiation. Although, in the embodiments described below, the light that is incident on the gratings or sensors is visible light, the light that is incident on the gratings or sensors of the present disclosure may be any type of electromagnetic radiation, including infrared light, ultraviolet light, etc., that may be scattered by a grating or sensor. Although, in the embodiments described below, the light that is scattered from the gratings or sensors and detected by a detector is visible light, the light that is scattered by a grating or sensor of the present disclosure and detected by a detector of the present disclosure may be any type of electromagnetic radiation, including infrared light, ultraviolet light, etc. that may be scattered by a grating or sensor.

For purposes of the present disclosure, the term "purified" refers to the component in a relatively pure state, e.g. at least about 90% pure, or at least about 95% pure, or at least about 98% pure.

For purposes of the present disclosure, the term "photoinitiator" refers to a molecule that creates reactive species such as free radicals, cations or anions when exposed to radiation such as UV or visible sources such as blue light, for example.

For purposes of the present disclosure, the term "room temperature" refers to a temperature of from about 20° C. to about 25° C.

For purposes of the present disclosure, the term "subject" refers to an entity which is the object of treatment, observation, or experiment. By way of example only, a "subject" may be, but is not limited to: a human, a mammal, a reptile, a bird, a fish, an amphibian, and an invertebrate.

For purposes of the present disclosure, the term "synergistic effect" refers to a combined effect when two or more substances or biological structures interact resulting in an overall effect that is greater than the sum of individual effects of any of the two or more substances or biological structures.

For purpose of the present disclosure, the term "substrate" or "surface" refers to any target for treatment, observation, or experiment under wet or dry condition. By way of example only, a "substrate" or "surface" may be, but is not limited to: a coral reef, wood, metal, glass, plastic, ceramic, tile, paper, skin, wound, and tissue.

For purposes of the present disclosure, the term "3D printing" refers to the action or process of making a physical object from a three-dimensional digital model which may typically include laying down many thin layers of a material in succession. In some embodiments, 3D printing, or additive manufacturing is the construction of a three-dimensional object such as from a CAD model or a digital 3D model that is converted into a G-code that provides the pathway to define the printed structure. It can be done in a variety of processes in which material is deposited, joined, or solidified under computer control, with the material being superposed layer-by-layer and added together (such as termo-plastics, viscous-liquids or compressed-powder grains being fused), typically layer by layer.

For purposes of the present disclosure, the term "underwater" refers to seawater.

Description

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Living organisms have managed to survive and thrive in their environment by developing their unique traits. In response to modern societies' needs and emerging ecological concerns, nature has inspired scientists to develop eco-friendly, life-changing materials. By imitating their biological systems, disclosed embodiments disclosed embodiments can create a bioinspired material to solve the disclosed complex scientific challenges, such as developing a water-based adhesive for high-salt environments.

Organisms, such as barnacles and mussels have evolved to produce and secrete materials that adhere under harsh conditions. These organisms developed byssus that offers extremely versatile adhesion, and they can stick to almost every substrate in diverse environmental conditions, including freshwater and seawater.[1] The byssus consists of proteins with high content of a modified amino acid, 3,4-dihydroxy-L-phenylalanine (DOPA, an amino acid with a catechol side chain), responsible for the adhesive properties.[2,3] Despite its excellent properties, extracting this adhesive substance requires approximately 10,000 mussels to obtain only one gram of product.[4] A different way to produce an adhesive protein is through recombinant protein expression in *E. Coli*. Unlike natural mussel adhesive proteins, the recombinant adhesive protein from bacteria does not contain DOPA residue in its sequence due to the lack of a post-translational modification mechanism.[5] Therefore, an enzyme treatment is needed to convert tyrosine to DOPA rendering the production unprofitable.[6] Consequently, developing a cost-effective catechol-based adhesive material that can offer enormous applications in medicine, biomedical engineering, nanotechnology, and many others is essential.[7]

Understanding catechol's role in adhesion motivated scientists to develop bioadhesive materials for applications in medicine, biomedical engineering, nanotechnology, and many others.[7] Generally, catechol moieties are introduced by a) functionalization of polysaccharides,[8-14] proteins,[15,16] polypeptides,[17,18] surfactants,[19] or synthetic polymers with catechol units,[20-22] b) polymerization of dopamine or dopamine methacrylamide and copolymerization with other conventional monomers.[23-25]

Interestingly, there is a pattern in the mussel foot proteins, where lysine (Lys) is often found in the protein sequence in a position close to DOPA. It has been also reported that the synergistic effect of the Lys residue promotes adhesion when it is near DOPA.[26-29] The enhanced adhesion, especially in the seawater, is a result of the synergy between the positively charged amines and the catechol moieties and is primarily attributed to the interaction of the catechols with the surfaces after the displacement of the salts by the cations. Besides that, the cation-π interactions of the functional groups contribute to the proteins' strong cohesive and mechanical properties.[30-32, 47-48] Unfortunately, synthesizing materials with Lys and DOPA residues in close proximity is often challenging and requires multiple steps.[33,34]

The present disclosure proposes a simple way to generate a bioinspired underwater adhesive using two main precursors of Lys-DOPA methacrylate (KDOPA-MA) as a monomer and Lys-DOPA dimethacrylate [$(KDOPA)_2$-DMA] as a crosslinker. KDOPA-MA was synthesized by Solid Phase Peptide Synthesis (SPPS) after methacrylation of N-terminus. $(KDOPA)_2$-DMA was synthesized in a similar way using a bifurcation molecule. Lys-tyrosine methacrylate (KY-MA), an analogue of the KDOPA-MA, was also synthesized for comparison. By exposing a mixture of DOPA precursors and photoinitiator in water with visible light, disclosed embodiments generated a strong adhesive that could be applied to various surfaces under wet conditions. Mechanical measurements were performed to evaluate the adhesiveness on different substrates. Developing an eco-friendly adhesive that can be applied underwater is of great importance since some of the commercially available adhesives, like cyanoacrylates, are either cytotoxic or immediately polymerized when they come in contact with water.[35,36] Compared to cyanoacrylates, the disclosed non-toxic the disclosed underwater adhesive can be applied in healthcare, particularly in wound healing as a temporary replacement of stitches and in coral reef restoration initiatives, like the micro-fragmentation approach.[37,38] This approach takes advantage of the enhanced coral growth rate of small fragments (usually in land-based nurseries) compared to the larger ones and then plants the micro fragments array back into the sea. A non-toxic, instant and underwater applicable glue can be potentially used in this application (FIG. 1).

In one embodiment, a compound comprises a structure of Formula 1,

Formula 1

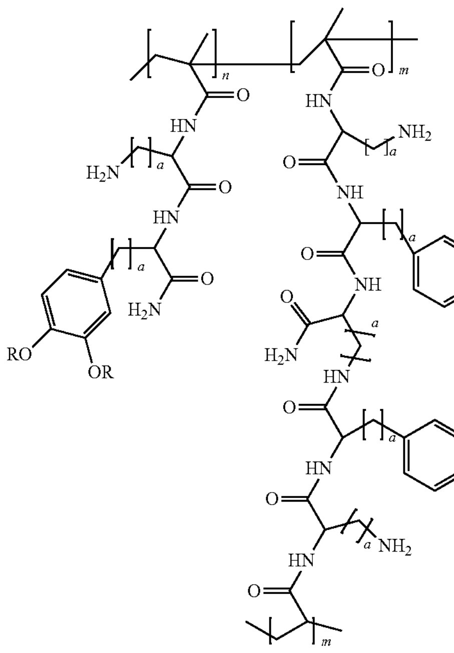

a is from 1 to 6. R is at least one selected from the group consisting of hydrogen, —O—$(CH_2)_b$, and $(CH_2)_b$. b is from 1 to 6. n is 3 to 8 times higher than m.

In one embodiment, a compound is a water-based photoreactive adhesive material and the compound is applied to a substrate under wet or dry condition.

In one embodiment, a wet condition is salt water or water.

In one embodiment, a compound comprises a structure of Formula 2,

Formula 2

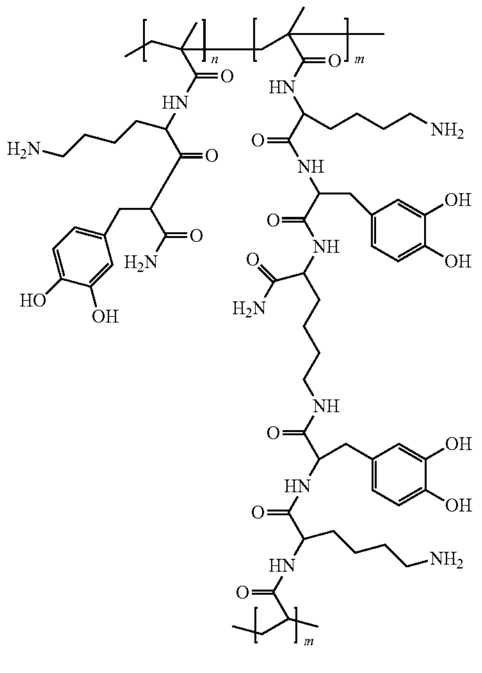

n is 3 to 8 times higher than m.

In one embodiment, n is 4 to 6 times higher than m.

In one embodiment, a method of manufacturing a peptide-based adhesive material comprises mixing an aqueous solution of a catechol-based monomer, a catechol-based cross-linker, and a photoinitiator to form a first solution, applying the first solution to a first substrate to form a second substrate, attaching a third substrate to the second substrate to form a fourth substrate, and exposing the fourth substrate to light to attach the first and the third substrate.

In one embodiment, a monomer is a Lys-DOPA methacrylate. A crosslinker is a Lys-DOPA dimethacrylate. Crosslinker:monomer:photoinitiator has an average molarity ratio in a range of 2:16:1 to 4:20:1. In some select embodiments, the monomer may be a methacrylated peptide with 1-6 amino acids. Lys may be replaced with a positive amino acid (Arg) and Dopa can be replaced with tyrosine (Tyr) or trihydroxyphenylalanine (TOPA). Additional or other amino acids may be selected. Tyr has one hydroxyl group, Dopa has two and Topa has three. Thus, derivatives of Dopa may be utilized. In preferred embodiments, to ensure proper adhesiveness disclosed embodiments will include, at least, Tyr, Dopa or Topa methacrylate.

In one embodiment, a photoinitiator is a lithium phenyl-2,4,6-trimethylbenzoylphosphinate (LAP). In some disclosed embodiments, any water-soluble photoinitiator can be used. Examples may include: Irgacure 2959, sodium 4-[2-(4-morpholino)benzoyl-2-dimethylamino]butylbenzenesulphone (MBS), Mono-acylphosphine oxides (MAPO), bi-sacylphosphine oxides (BAPO), 2,2'-azobis[2-methyl-N-(2-hydroxyethyl) promionamide](VA-086) and others.

In one embodiment, a first solution is applied to a first substrate under wet or dry condition.

In one embodiment, a fourth substrate is exposed to light for 5 to 60 seconds.

In one embodiment, a fourth substrate is exposed to light for 10 to 30 seconds.

In one embodiment, a fourth substrate is exposed to UV light or visible light, such as blue light, for example.

In one embodiment, a fourth substrate is exposed to 240-450 nm wavelength light.

In one embodiment, a fourth substrate is exposed to 395-400 nm wavelength light.

In one embodiment, a method of attaching a tissue comprises applying an effective amount of a first solution to a first tissue of a subject to form a second tissue, attaching a third tissue to the second tissue to form a fourth tissue, and exposing the fourth tissue to light to attach the first and the third tissue. The subject is selected from the group consisting of a human, a mammal, a reptile, a bird, a fish, an amphibian, and an invertebrate.

In one embodiment, a method of microfragmenting comprises applying an effective amount of a first solution to a first substrate to form a second substrate, attaching a third substrate to the second substrate to form a fourth substrate, and exposing the fourth substrate to light to attach the first and the third substrate. The substrate is a coral reef.

In one embodiment, a method of applying a peptide-based adhesive material comprises applying an effective amount of a first solution to a first surface to form a second surface, attaching a third surface to the second surface to form a fourth surface, and exposing the fourth surface to light to attach the first and the third surface. The surface is at least one selected from the group consisting of dry surface, salt water contacted surface, and water contacted surface.

In one embodiment, a kit comprises an effective amount of a first solution. A first substrate is adhesive to a second substrate after an exposure to UV light or visible light.

In one embodiment, a device for applying a peptide-based adhesive material. The device comprises an effective amount of a first solution. A first substrate is adhesive to a second substrate after an exposure to UV light or visible light.

In one embodiment, a device is selected from the group consisting of a container with a dropper/closure device, a squeeze bottle pump spray, and an airless and preservative-free spray, and an injectable device.

Results and Discussion

Figure 2:
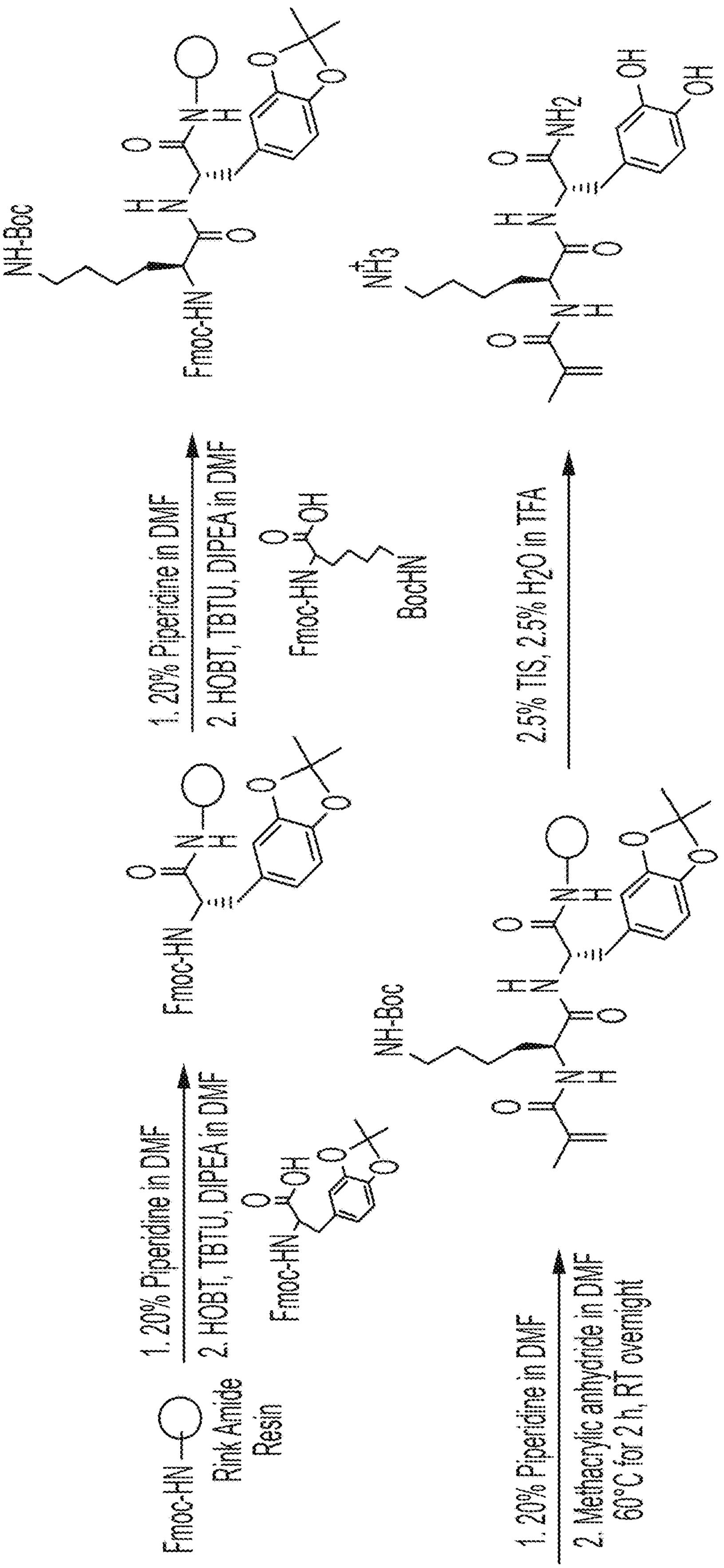
FIG. 2 illustrates synthesis of KDOPA-MA monomer according to one embodiment of the present disclosure.
Figure 3:
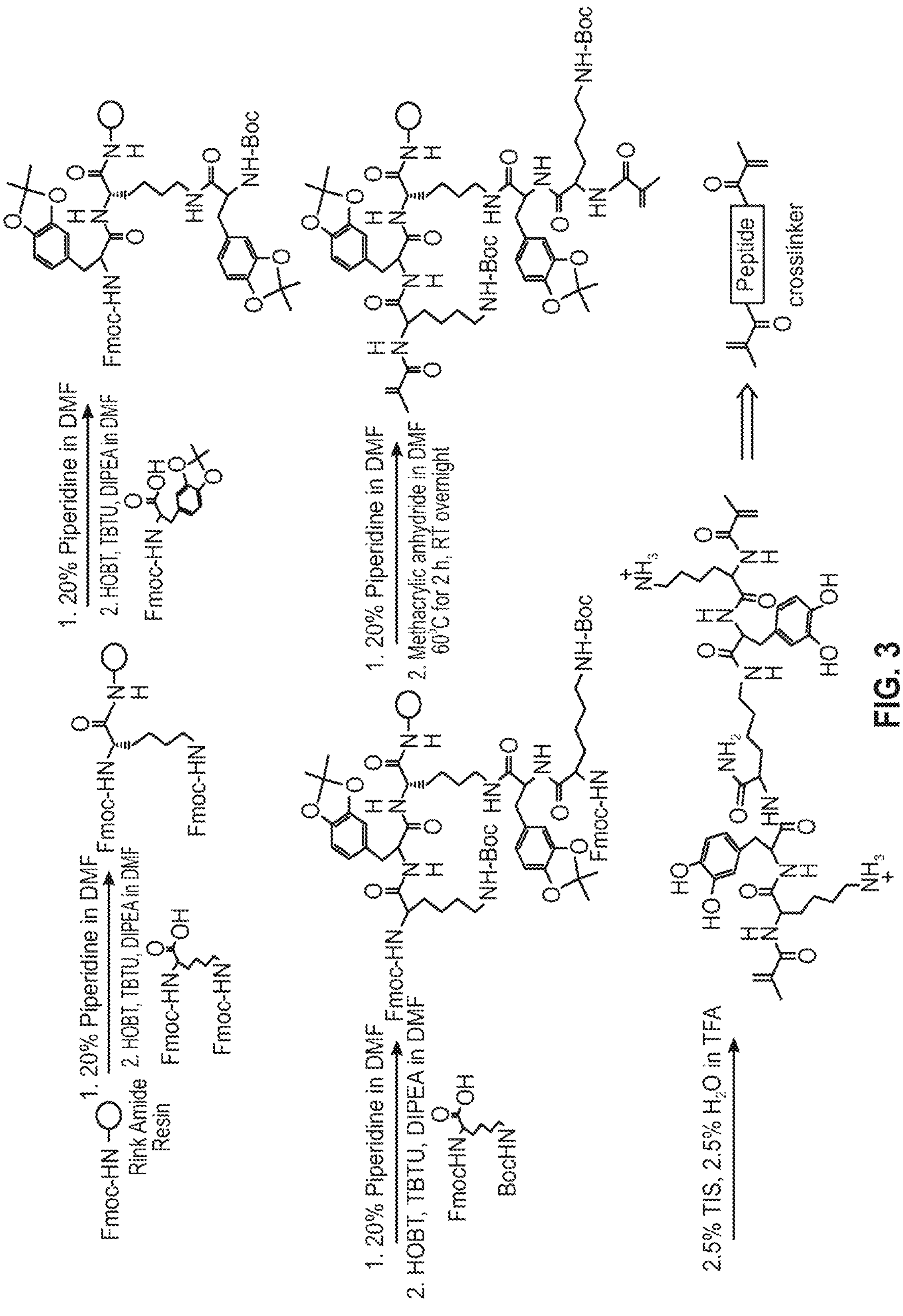
FIG. 3 illustrates synthesis of $(KDOPA)_2$-DMA crosslinker according to one embodiment of the present disclosure.
Figure 4:
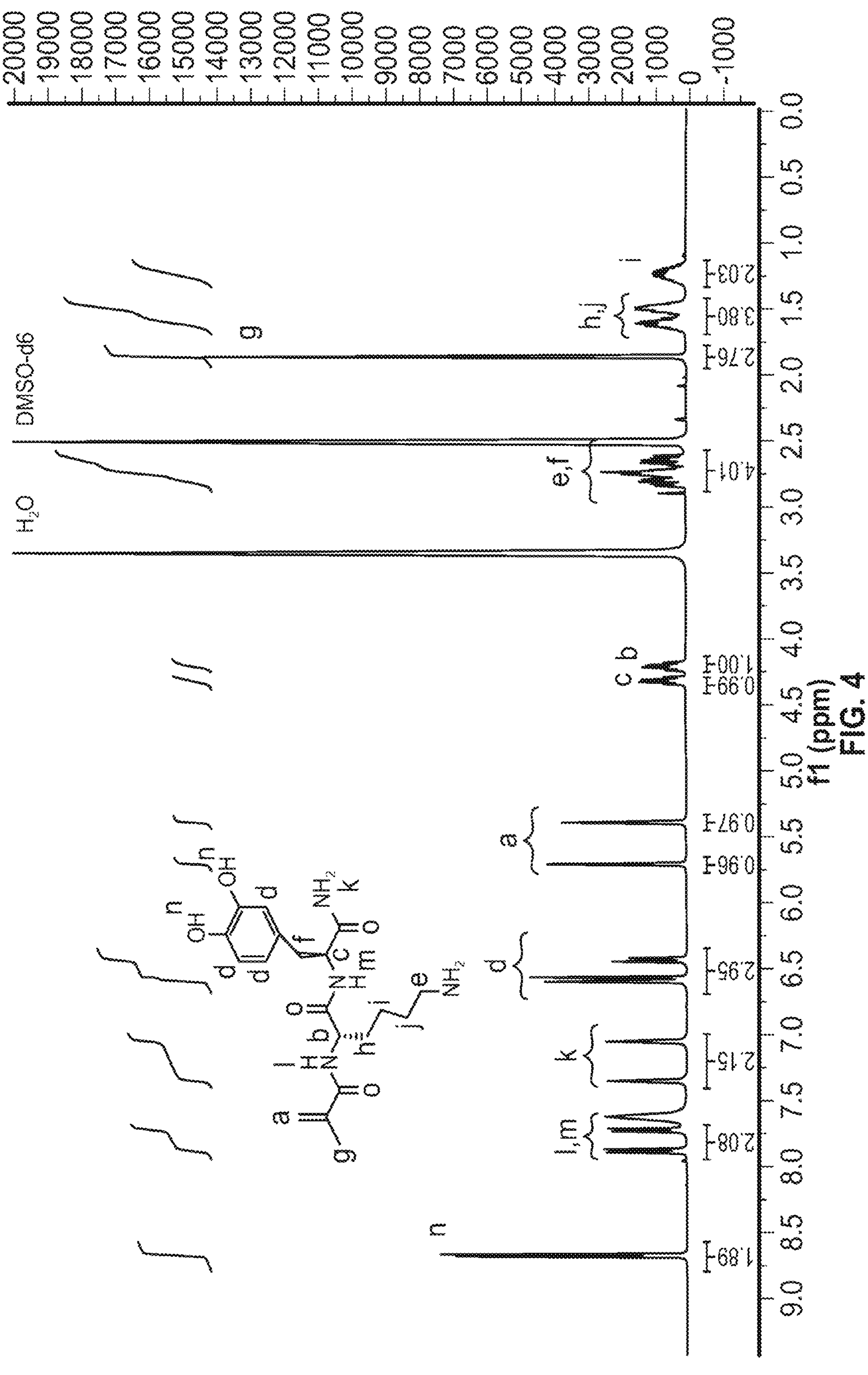
FIG. 4 illustrates $^1H$ NMR spectrum of the Lys-DOPA methacrylate (KDOPA-MA) according to one embodiment of the present disclosure.
Figure 5A:
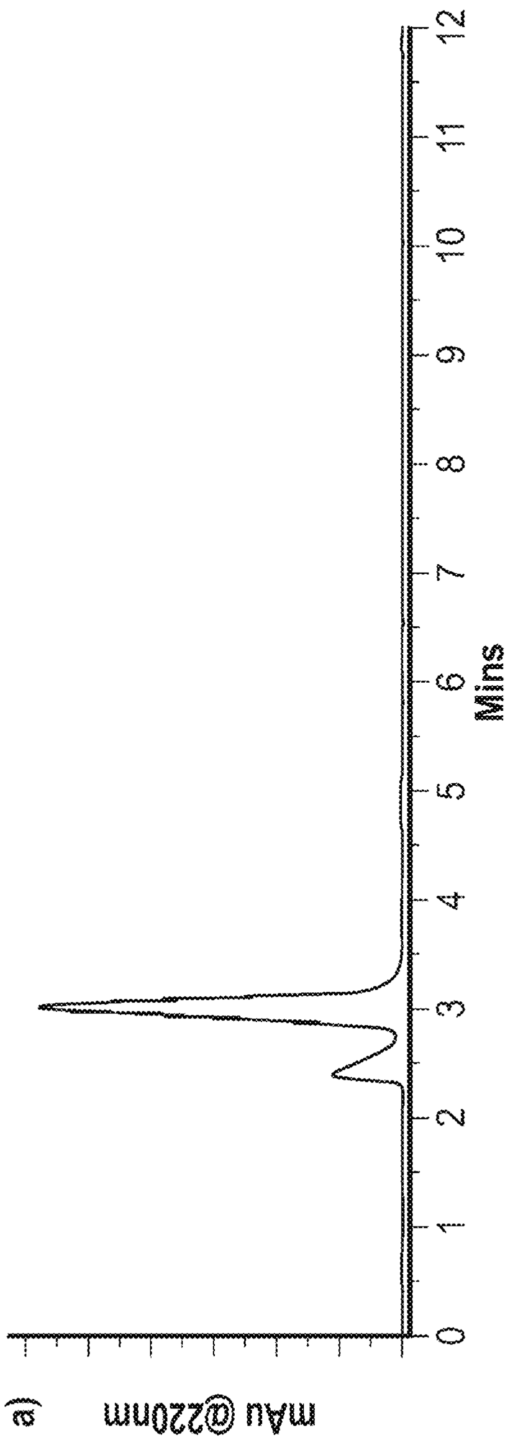
FIGS. 5A-5B illustrate LC-MS spectra of KDOPA-MA according to one embodiment of the present disclosure.
Figure 5B:
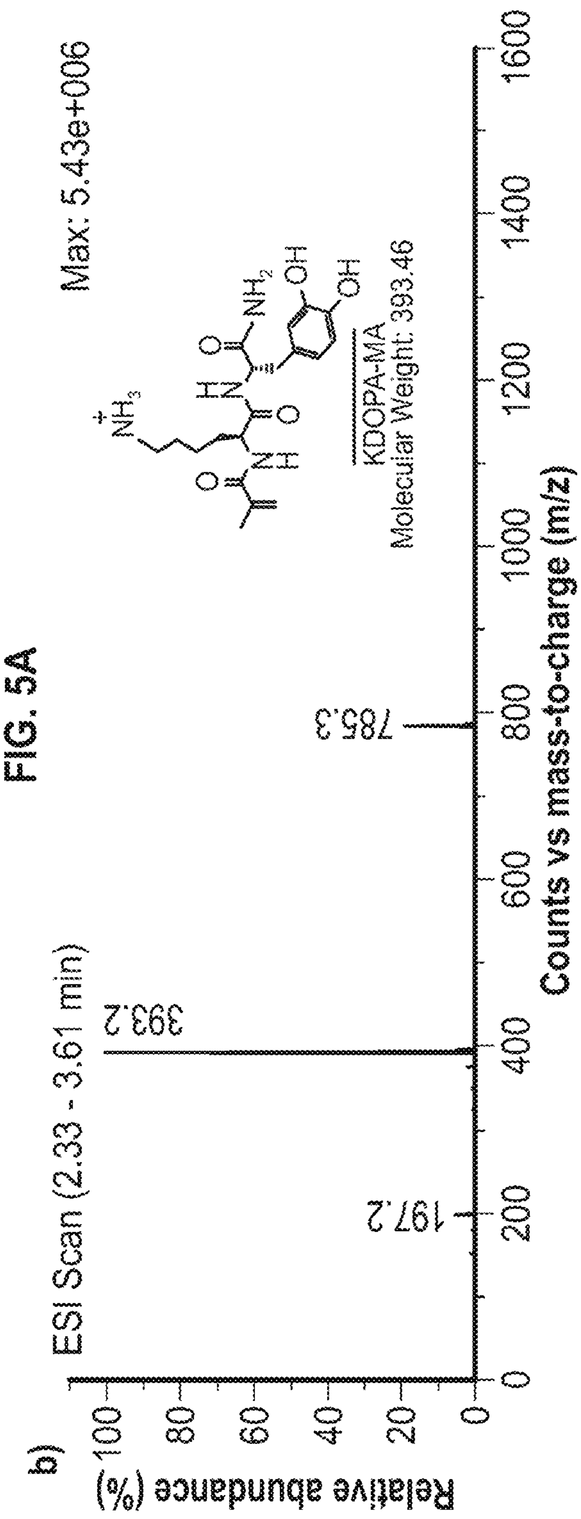
Figure 6:
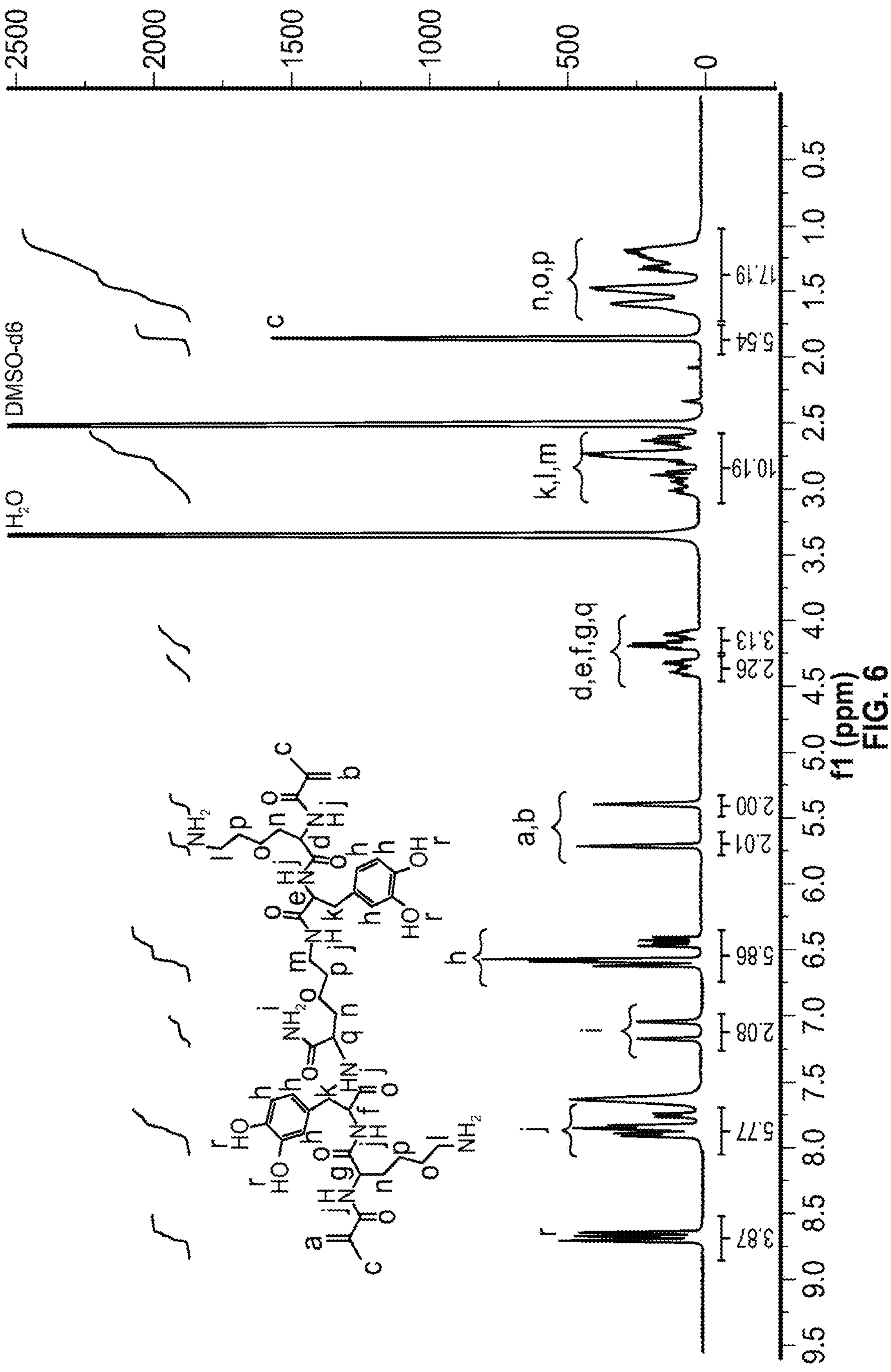
FIG. 6 illustrates $^1H$ NMR spectrum of the Lys-DOPA dimethacrylate [$(KDOPA)_2$-DMA]according to one embodiment of the present disclosure.
Figures 7A, 7B:
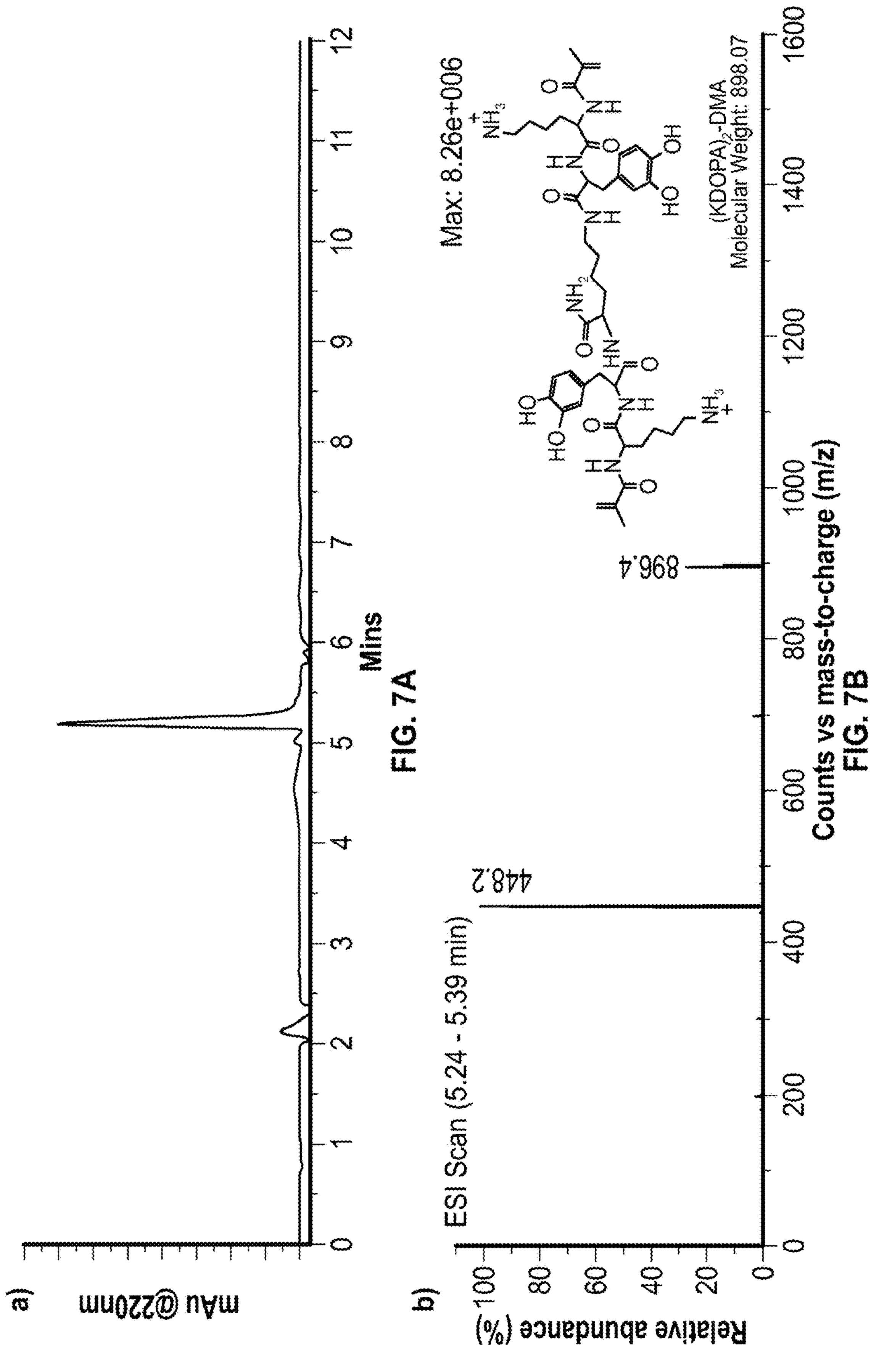
FIGS. 7A-7B illustrate LC-MS spectra of $(KDOPA)_2$-DMA according to one embodiment of the present disclosure.
Figure 8:
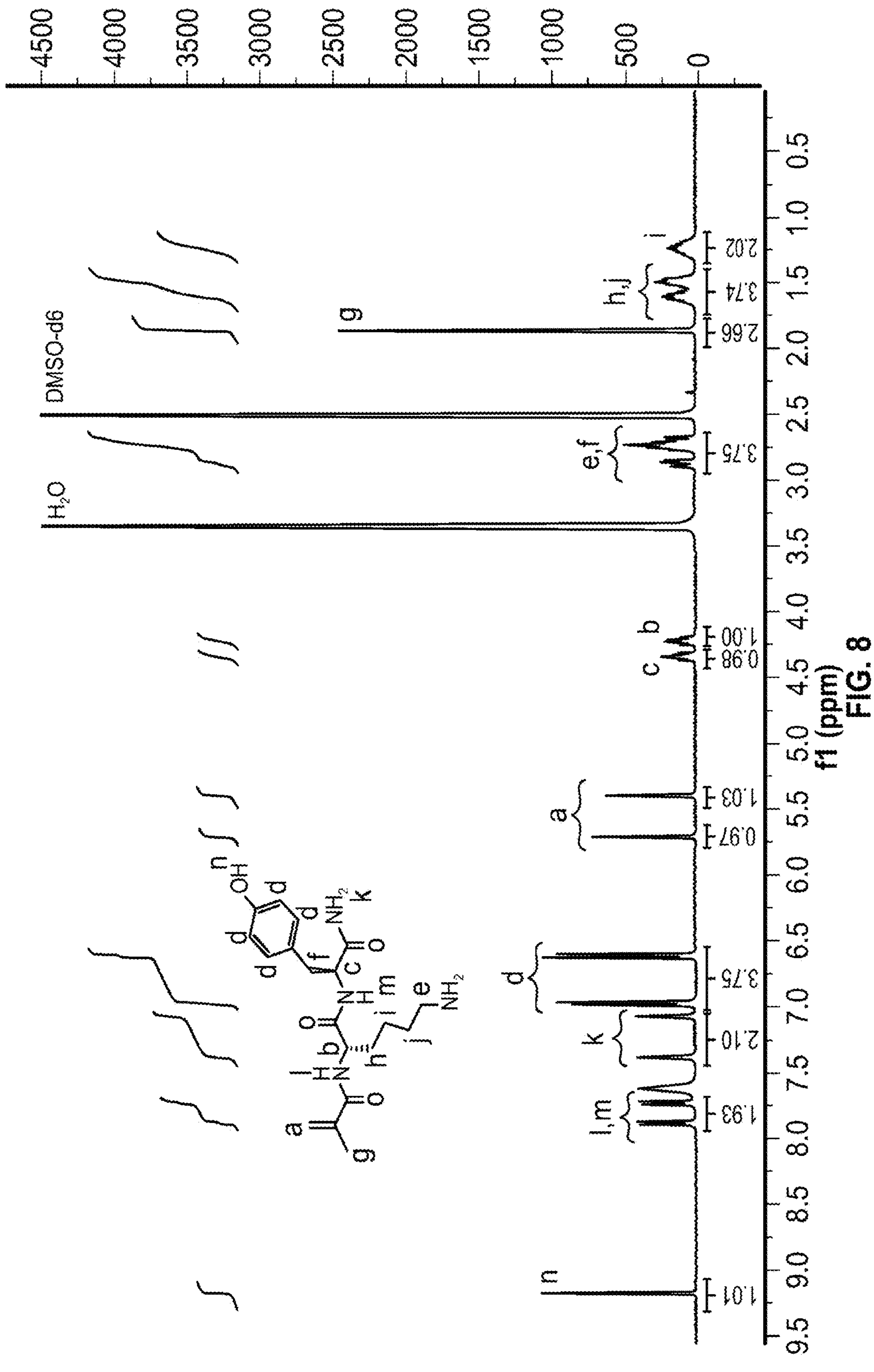
FIG. 8 illustrates $^1H$ NMR spectrum of the Lys-Tyr methacrylate (KY-MA) according to one embodiment of the present disclosure.

Inspired by the amino acid sequence pattern found in mussel foot proteins responsible for the excellent underwater adhesive properties, disclosed embodiments aimed to synthesize an eco-friendly adhesive consisting exclusively of the two amino acids, Lys and DOPA. In this direction a monomer KDOPA-MA was synthesized by SPPS and reaction of N-terminus with methacrylic anhydride (FIG. 2). The same synthetic procedure was used to synthesize KY-MA for comparison. To form a crosslinked polymeric network leading to enhanced mechanical properties, a crosslinking agent is needed. Following the same approach and by using Fmoc-Lys(Fmoc)-OH as bifurcation molecule, $(KDOPA)_2$-DMA was synthesized (FIG. 3). The successful synthesis of the three compounds was confirmed by $^1$NMR and LC-MS (FIGS. 4, 5A-5B, 6, 7A-7B, and 8). FIG. 5A illustrates Liquid chromatogram of KDOPA-MA absorption at 220 nm. FIG. 5B illustrates Mass spectrum of KDOPA-MA. MS: (m/z) calculated 393.46, $[M+H]^+$ found 393.2, $[2M+H]^+$ found 785.3, and $[M+2H]^{2+}$ found 197.2. FIG. 7A illustrates Liquid chromatogram of $(KDOPA)_2$-DMA absorption at 220 nm. FIG. 7B illustrates Mass spectrum of $(KDOPA)_2$-DMA. MS: (m/z) calculated 898.07, $[M+H]^+$ found 896.4, and $[M+2H]^{2+}$ found 448.2.

Figure 9:
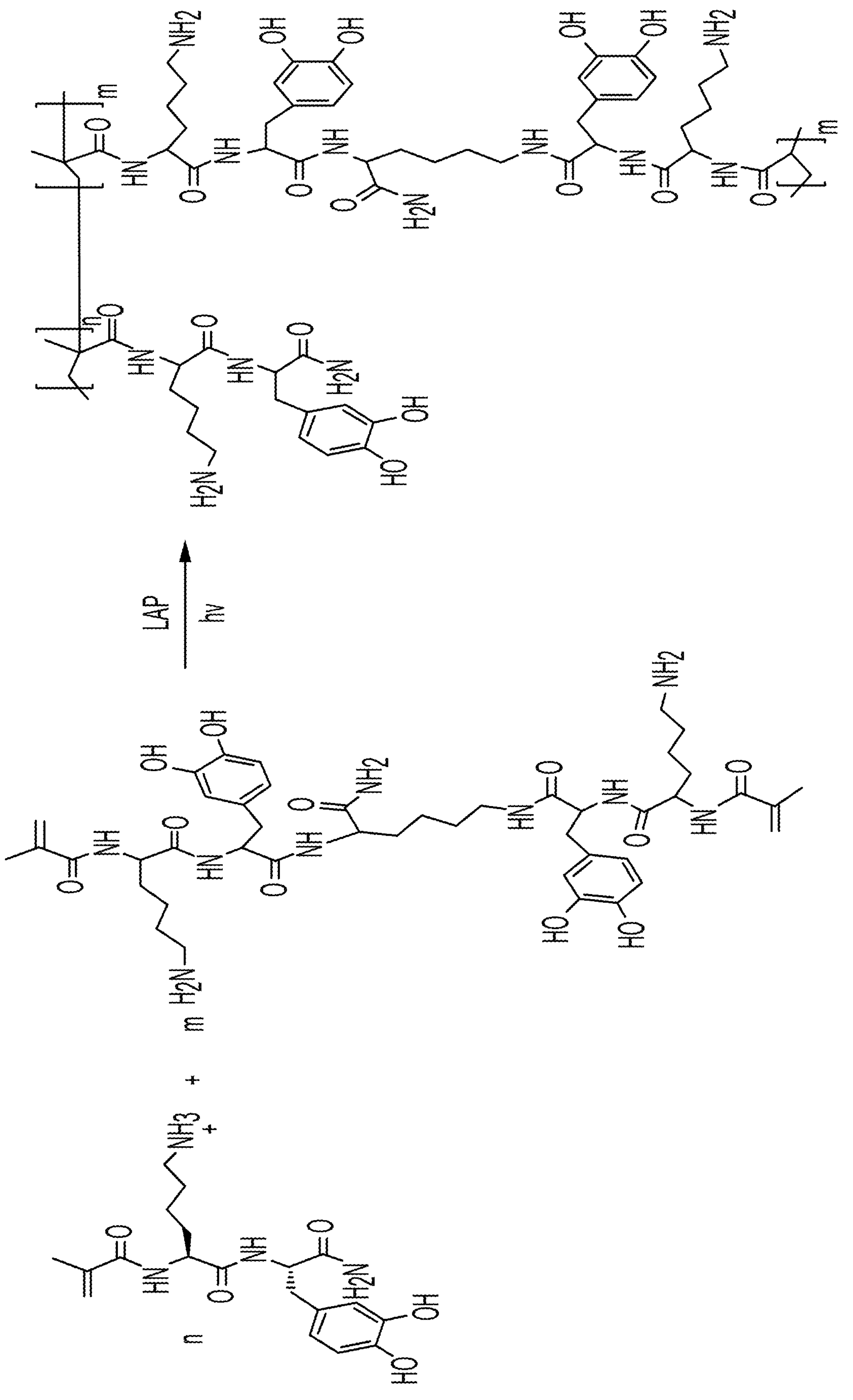
FIG. 9 illustrates a photopolymerization of KDOPA-MA and $(KDOPA)_2$-DMA in water according to one embodiment of the present disclosure.
Figure 10A:
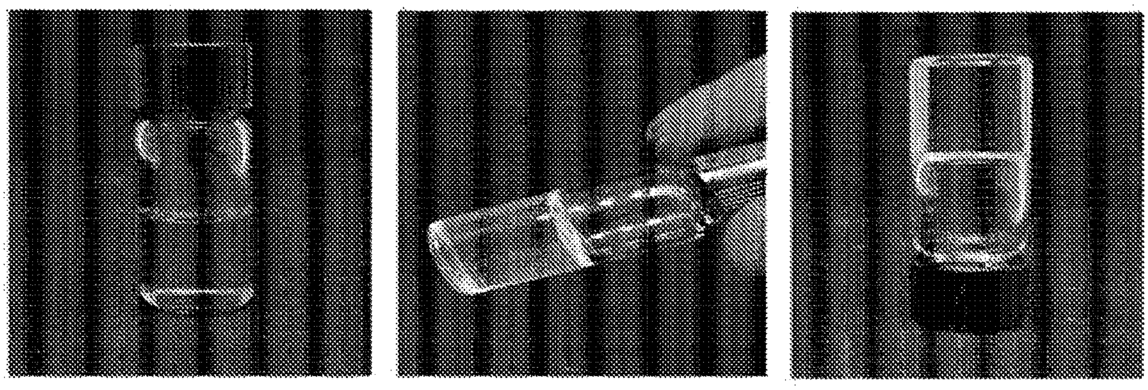
FIGS. 10A-10B illustrate inverted vial test before and after curing in 1 mL aqueous solution according to one embodiment of the present disclosure.
Figure 10B:
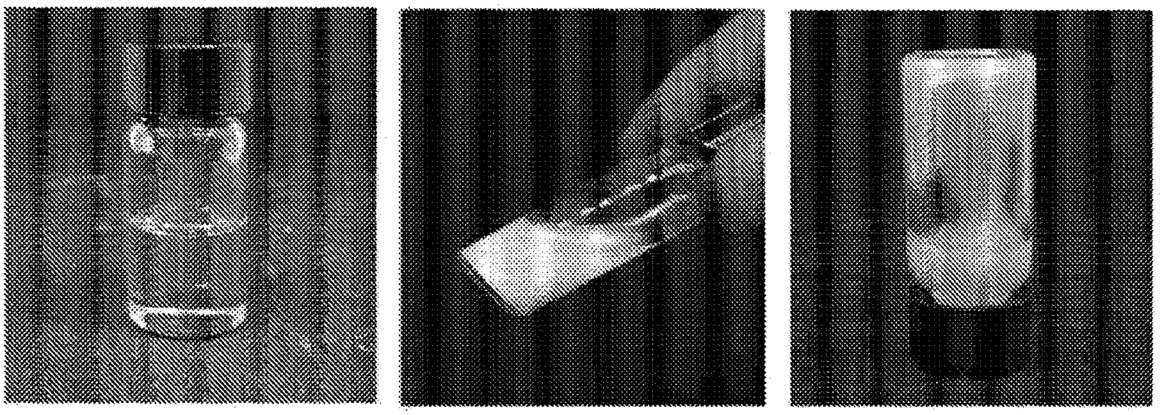
Figure 11A:
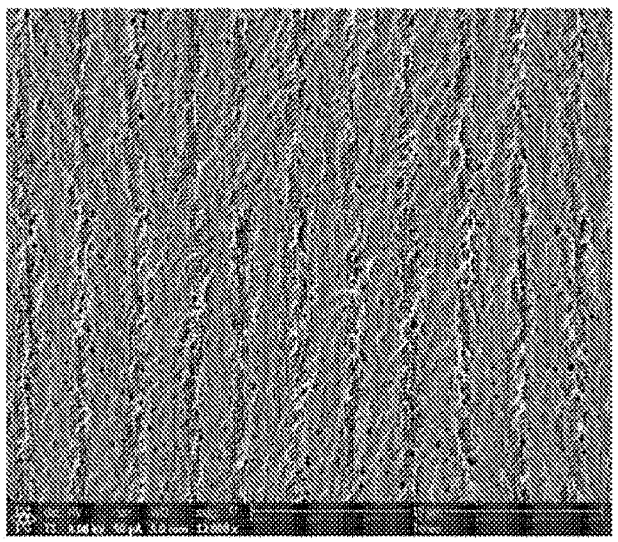
FIGS. 11A-11B illustrate SEM micrographs of KDopa adhesive with different crosslinker molar ratios compared to the monomer according to one embodiment of the present disclosure.
Figure 11B:
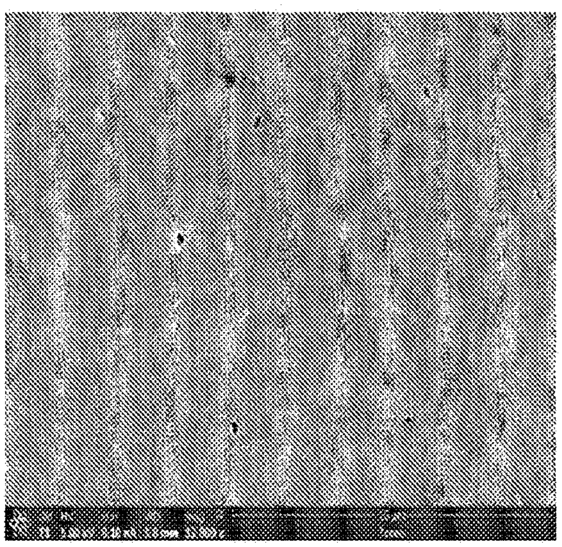

The minimum concentration of the monomer and the crosslinker that leads to a solid material after curing is 892.8 mM and 161.8 mM, respectively. The high hydrophilicity of both compounds allows the formation of a highly concentrated aqueous solution. After the photoinitiator (LAP) addition and the application of 395 nm wavelength light, radicals are formed, and a polymeric crosslinked network is created according to the reaction (FIG. 9). The solution solidifies after 10 sec of exposure to the UV light (FIGS. 10A-B). FIG. 10A has a vial (892.8 mM KDOPA-MA and 161.8 mM $(KDOPA)_2$-DMA) and FIG. 10B (297.6 mM KDOPA-MA and 53.9 mM $(KDOPA)_2$-DMA). In both cases, the LAP concentration was constant (50.9 mM) and the UV light was applied for 10 sec. When the concentration of the compounds decreases, the solution remains liquid and becomes cloudier after curing. Even though all the compounds are hydrophilic, disclosed embodiments assume that insoluble crosslinked aggregates (nanogels) form in lower concentrations, decreasing the solution transparency.[49] SEM image with 15% crosslinker molar ratio reveals a porous morphology for the dried glue after curing (FIG. 11A). The effect of the crosslinker's molar ratio on the morphology of the polymeric network is evident in FIG. 11B, where the pore sizes are significantly smaller when 45% molar ratio was used. FIG. 11A illustrates 15% crosslinker molar ratio. FIG. 11B illustrates 45% crosslinker molar ratio.

Figure 12A:
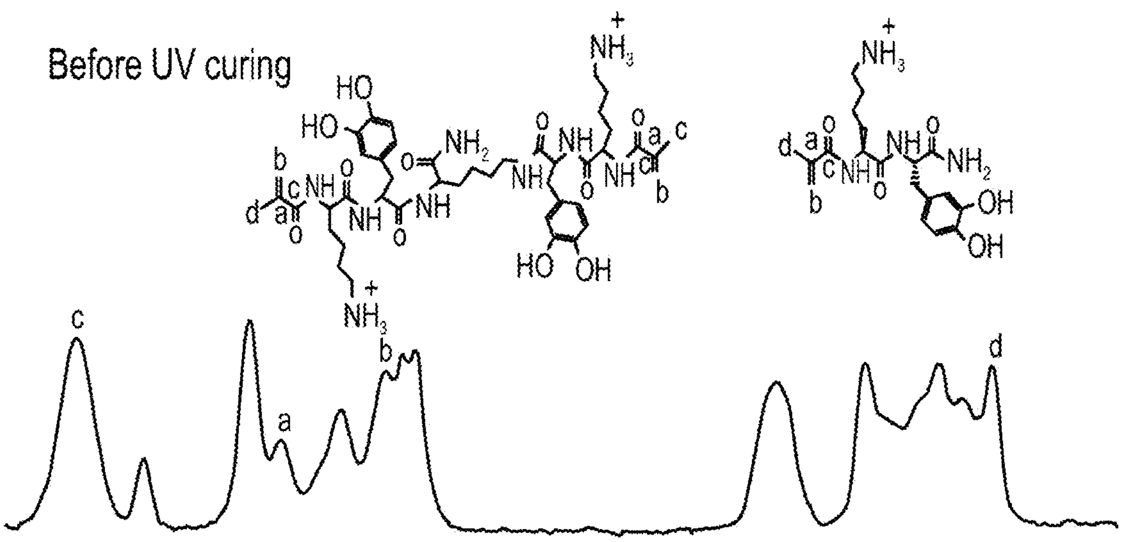
FIGS. 12A-12B illustrate $^{13}C$ MAS NMR spectra of dried KDopa adhesive before and after UV curing according to one embodiment of the present disclosure.
Figure 12B:
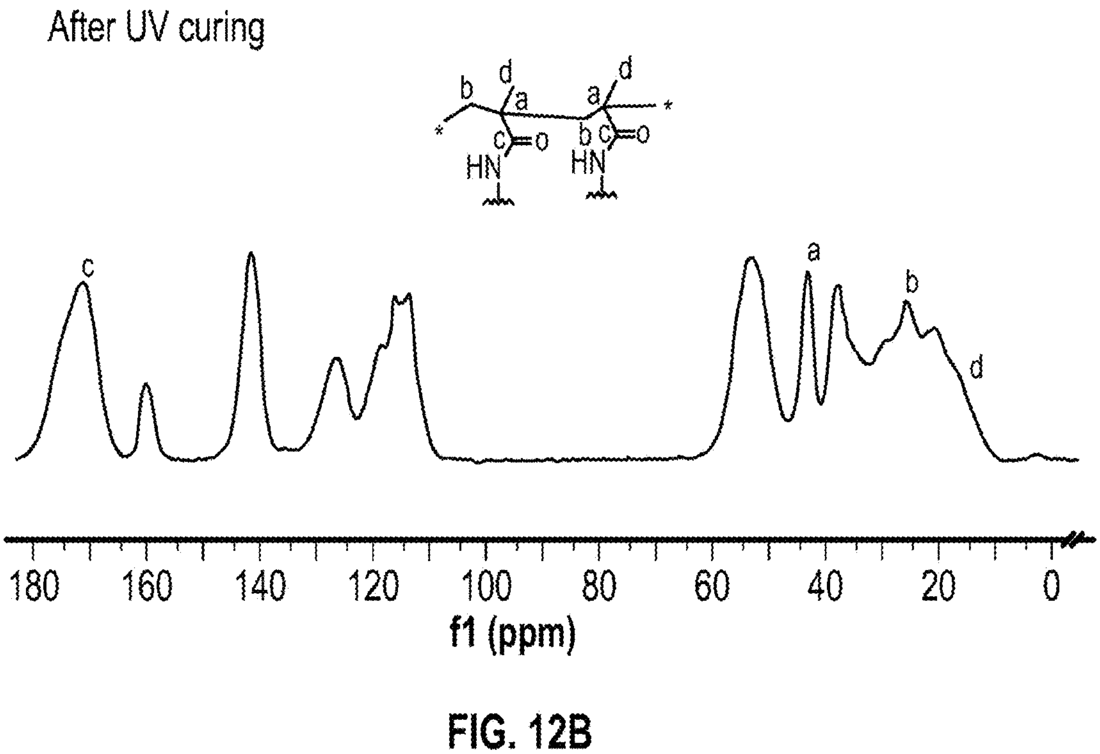
Figure 13:
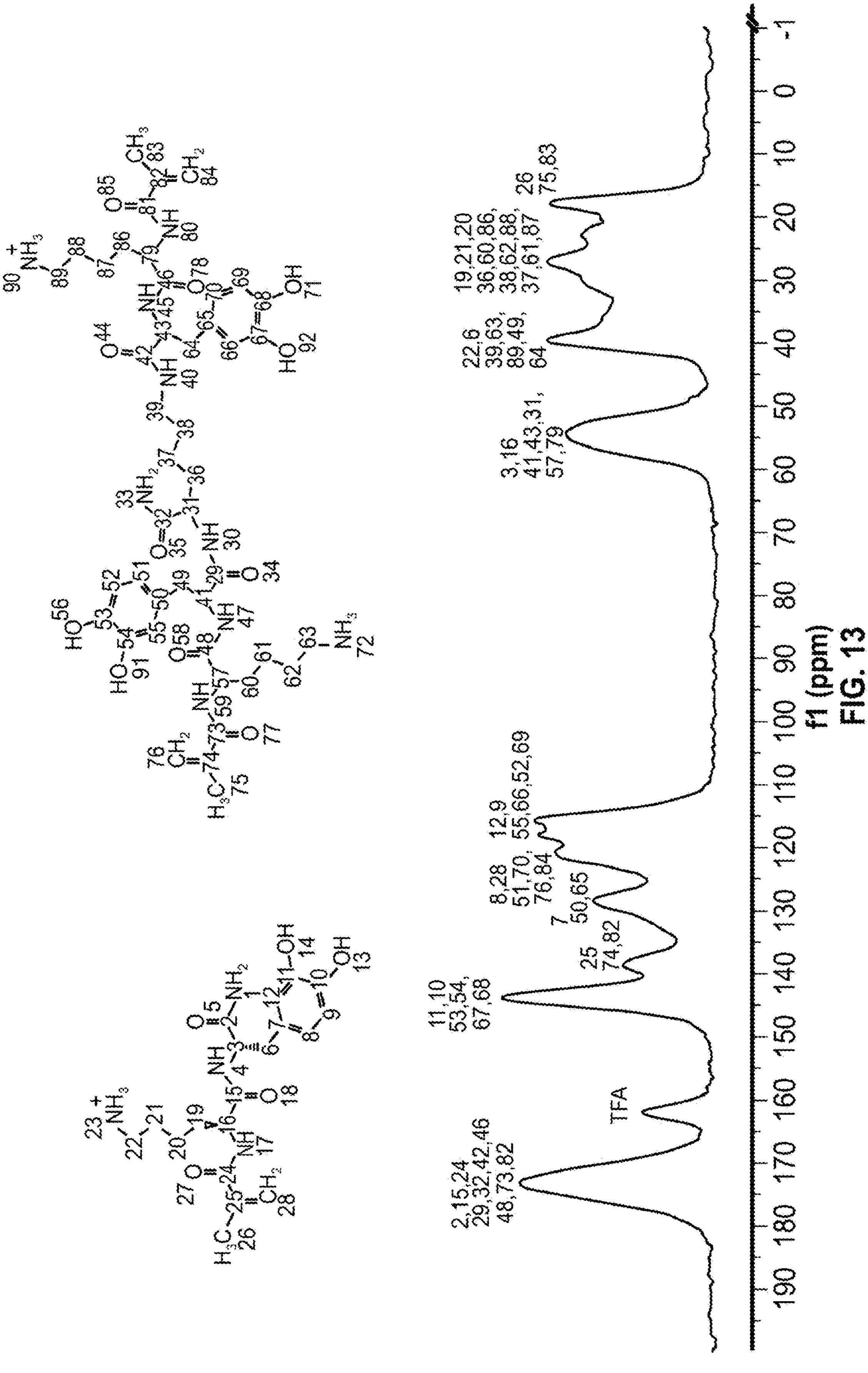
FIG. 13 illustrates $^{13}C$ solid-state NMR spectrum of the adhesive solution before UV curing according to one embodiment of the present disclosure.
Figure 14:
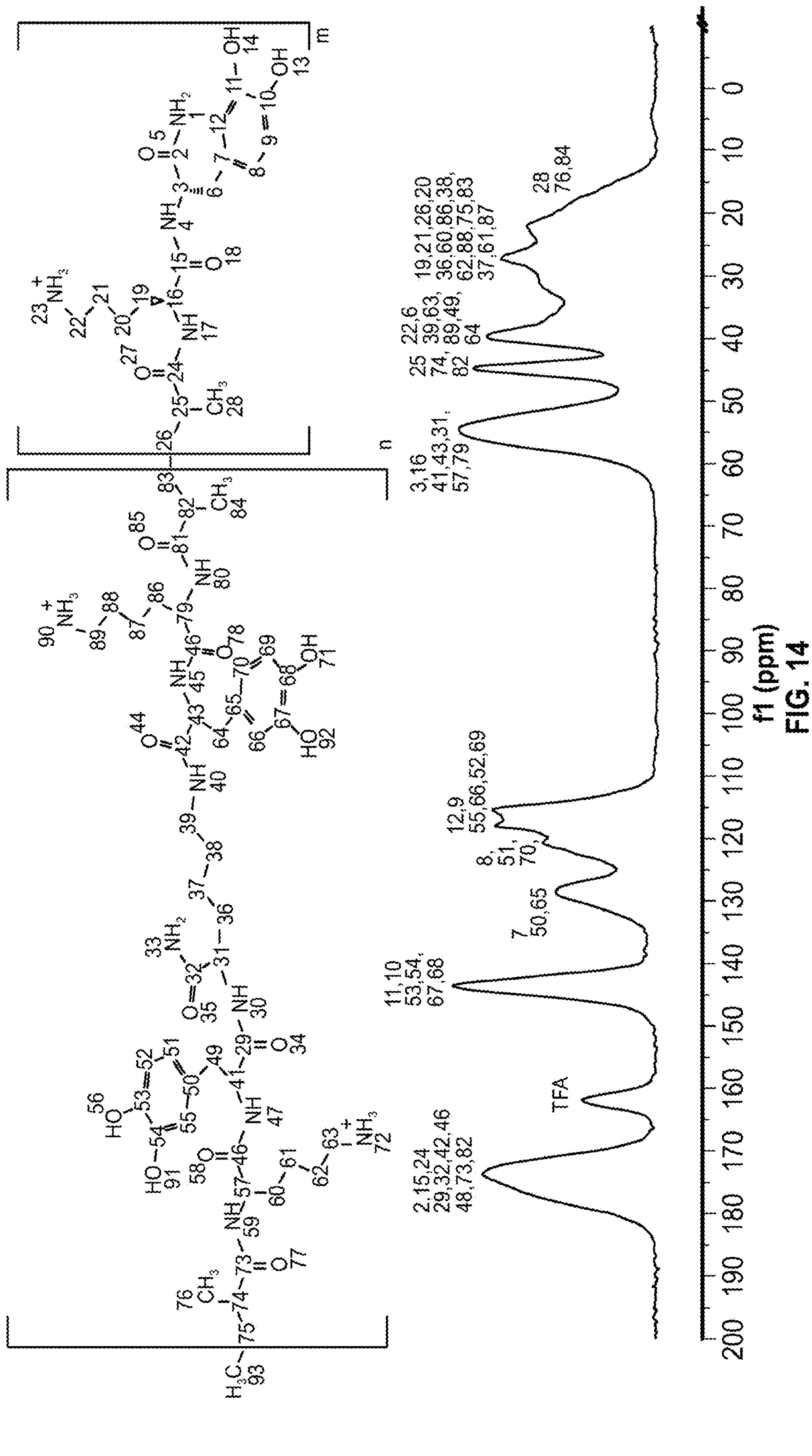
FIG. 14 illustrates $^{13}C$ solid-state NMR spectrum of the adhesive solution after UV curing according to one embodiment of the present disclosure.
Figure 15:
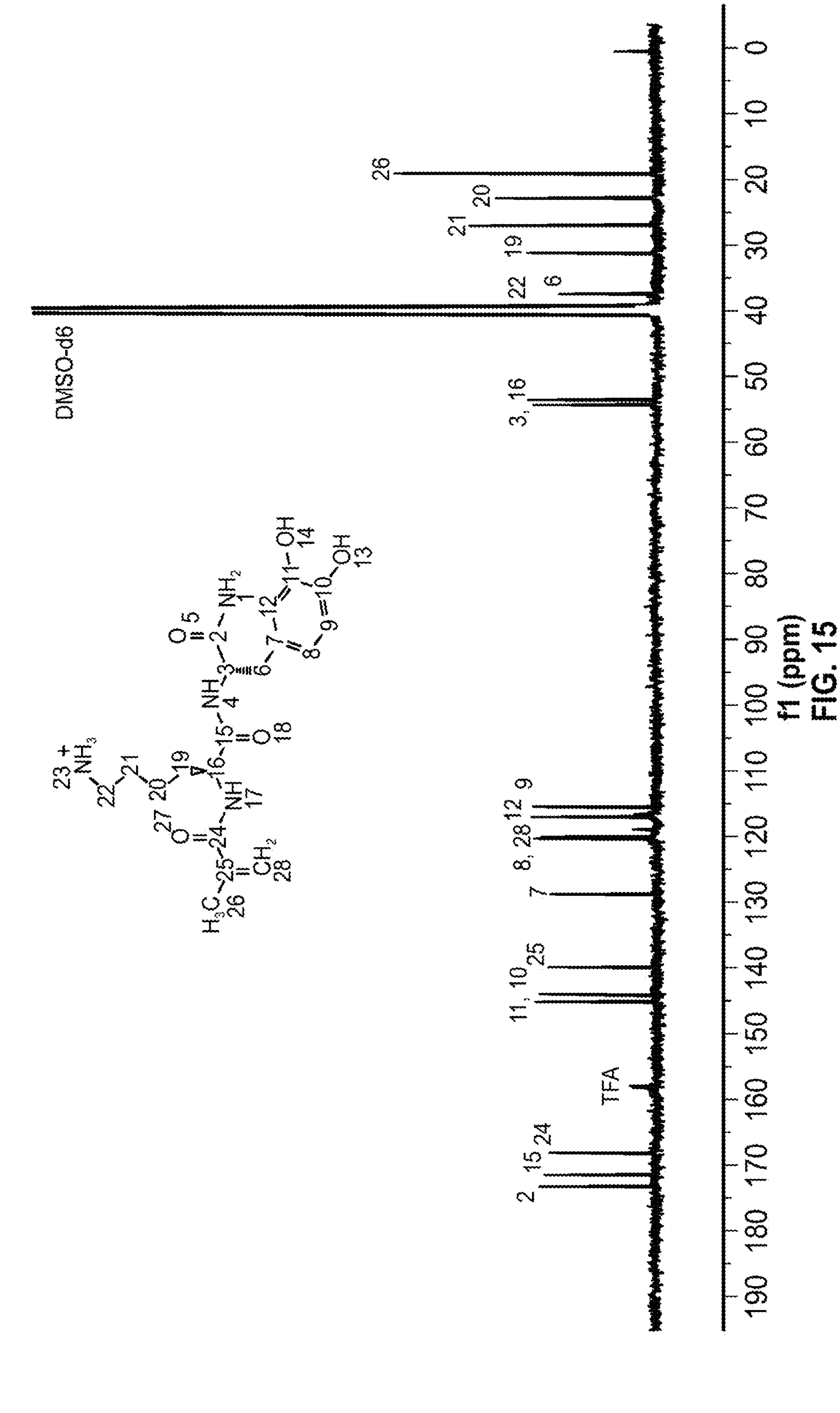
FIG. 15 illustrates $^{13}C$-NMR spectra of the KDOPA-MA monomer according to one embodiment of the present disclosure.
Figure 16:
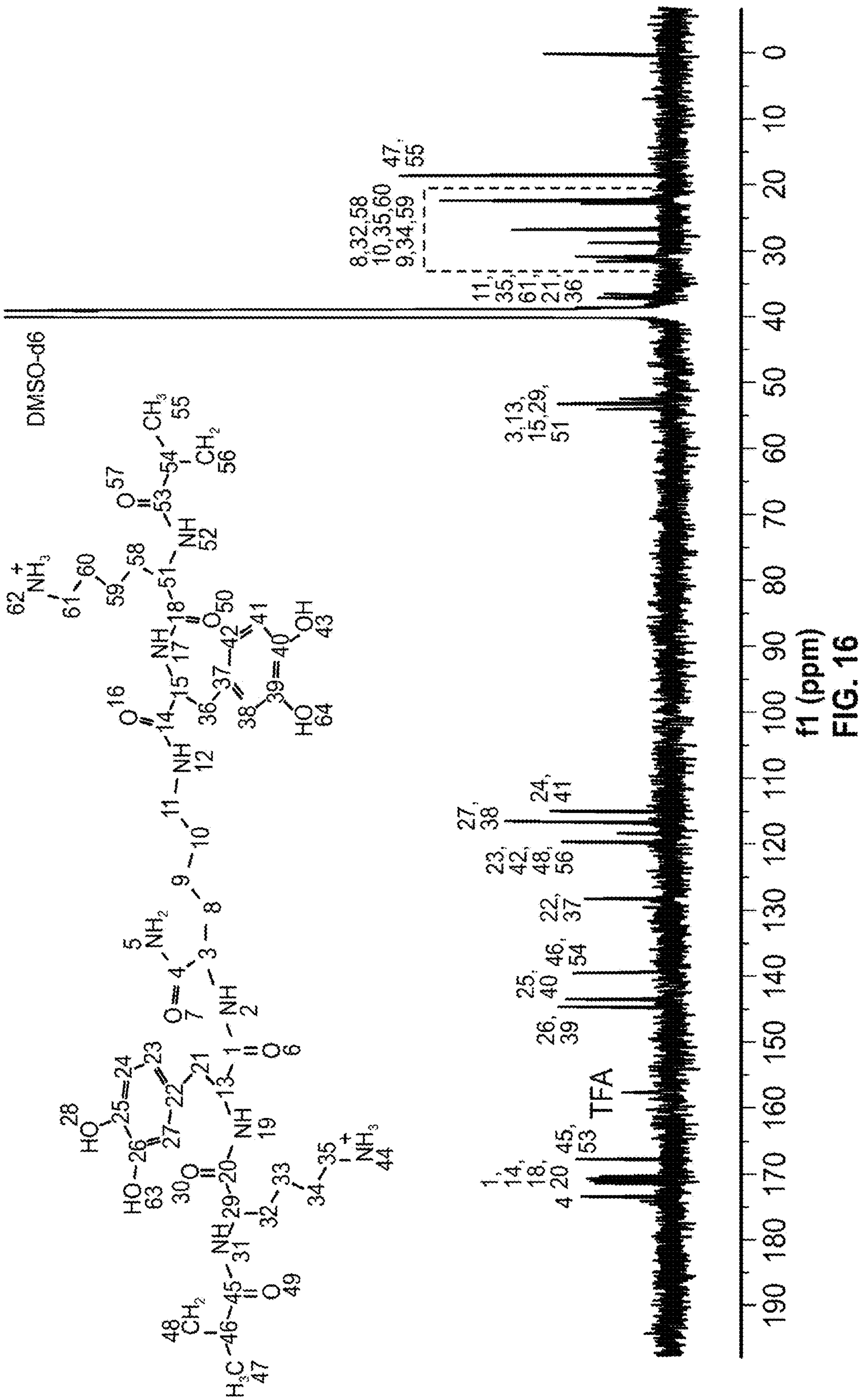
FIG. 16 illustrates $^{13}C$-NMR spectra of the $(KDOPA)_2$-DMA crosslinker according to one embodiment of the present disclosure.

The photopolymerization reaction of the peptide-based compounds was investigated using $^{13}C$ solid-state NMR spectroscopy (FIGS. 12A-12B and 13-14). As shown in FIGS. 12A-12B, the differences between $^{13}C$ magic-angle spinning (MAS) NMR spectra of dried samples before (FIG. 12A) and after UV curing (FIG. 12B) can be distinguished clearly. The resonance at 139 ppm and 128 ppm, which originate from carbon atoms (a) and (b) of the double bond of methacryloyl group, shift to 45 ppm and between 20-34 ppm, upon curing. A broad resonance of amide bond between 165-185 ppm also appears after UV curing due to the deshielding of amide atom (c). On the other hand, a shielding effect is observed for the peak that belongs to methyl carbon (d) of methacryloyl group. These changes in the chemical shifts indicate the main role of methacryloyl group during the photopolymerization. To confirm that these resonances originate from the methacryloyl group, $^{13}C$ NMR of peptide monomer, crosslinker, and photoinitiator in DMSO-d6 were performed (FIGS. 15-16).

Figure 17A:
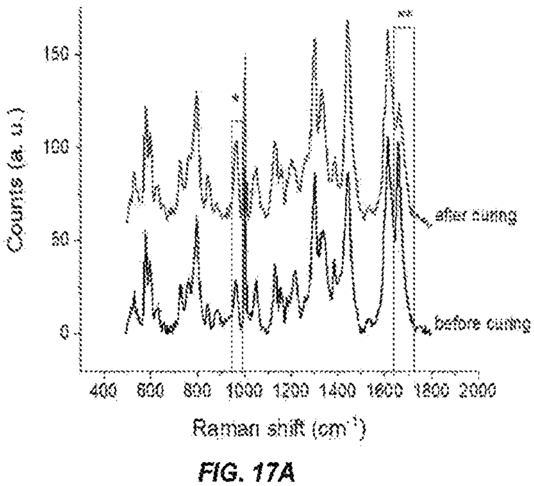
FIG. 17A-17C illustrates Raman spectra of the mixture before and after UV curing according to one embodiment of the present disclosure.
Figure 17B:
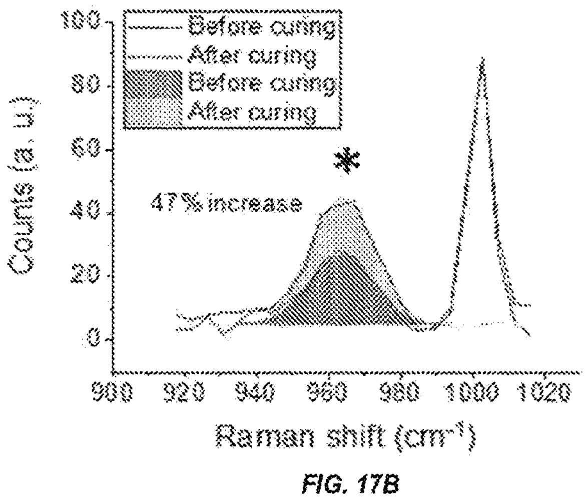
Figure 17C:
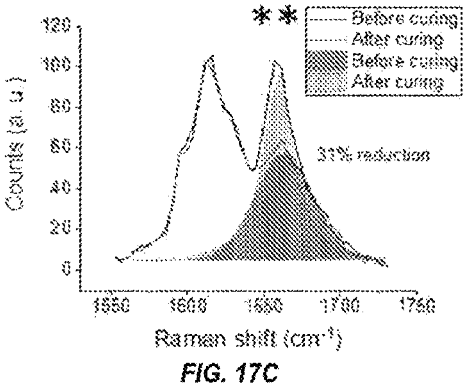
Figure 18A:
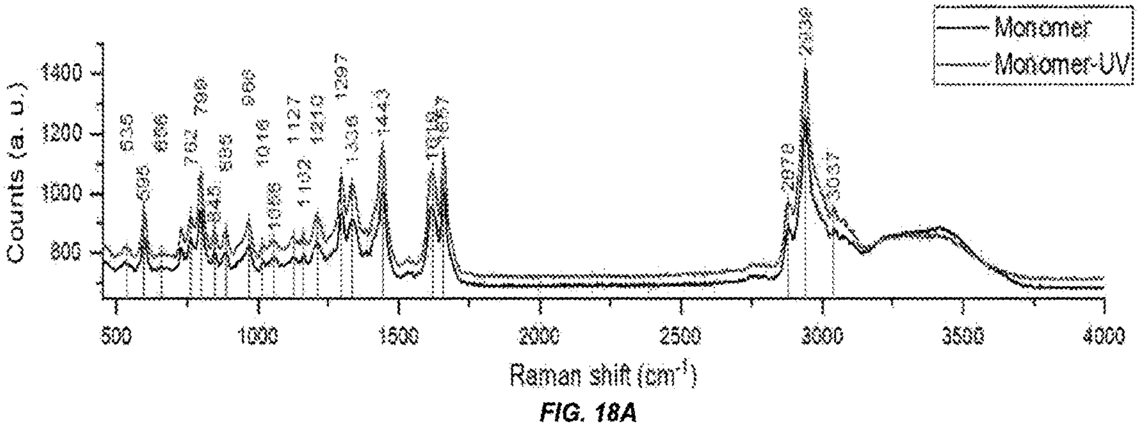
FIGS. 18A-18D illustrate Raman spectra of individual molecules composing the glue and the mixture without initiator before and after curing, with peak assignments monomer, crosslinker, initiator, and a mixture of monomer and crosslinker without initiator according to one embodiment of the present disclosure.
Figure 18B:
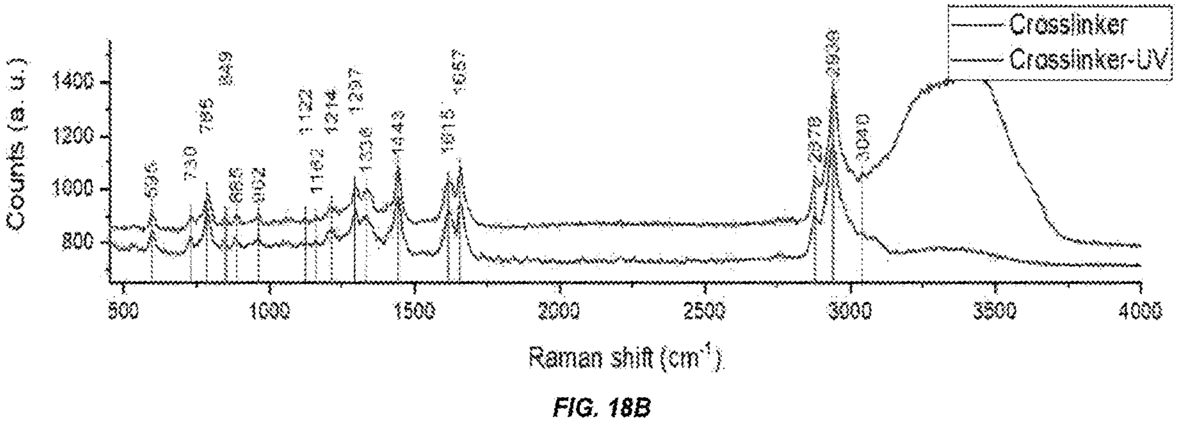
Figure 18C:
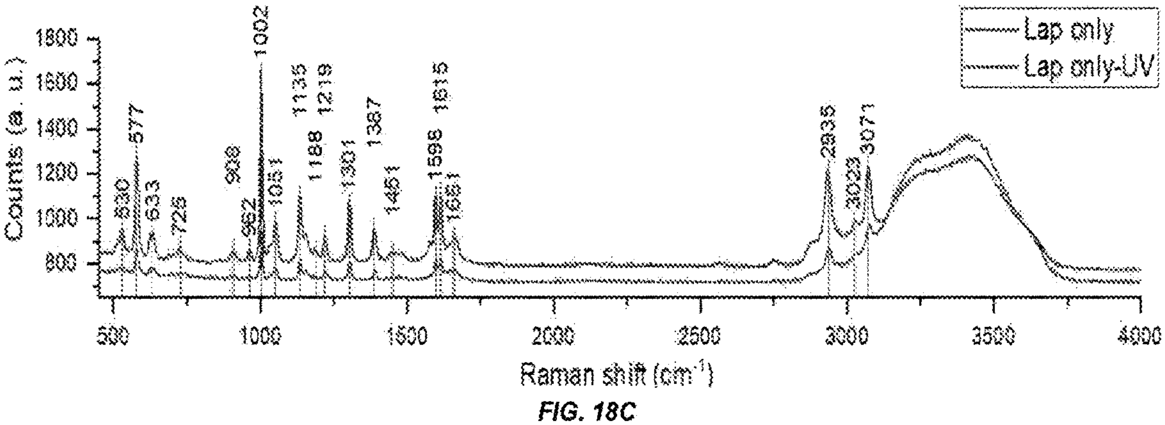
Figure 18D:
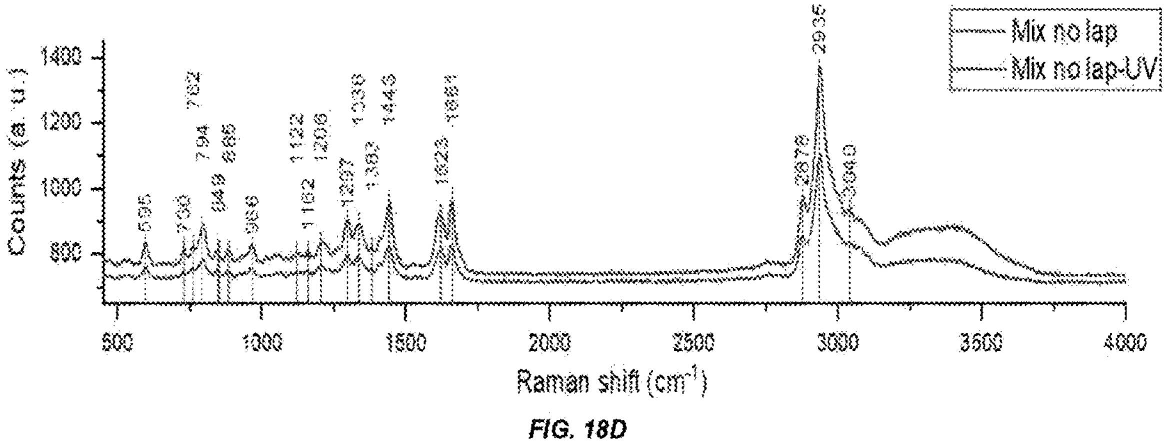

The adhesive's composition before and after the curing process was also evaluated by Raman spectrometry. Solutions of individual molecules were measured independently, and in a mixture before and after the photopolymerization. A mixture of molecules with the formulation described above was used as the adhesive and therefore measured to identify peaks related to crosslinking after curing. Negative control was the previous mixture of monomer and crosslinker without initiator. Several peaks can be noted in the single components of the mixture (FIGS. 17A and 18A-18D). FIG. 17A illustrates Raman spectra of the mixture before (bottom-black line) and after UV curing (top-blue line). FIG. 17B illustrates fitting of the peak at about 966 $cm^{-1}$ (*) before and after curing. FIG. 17C illustrates fitting of the peak at about 1660 $cm^{-1}$ (**) before and after curing. The red rectangle indicates the peaks related to v(C—C) (*), at about 966 $cm^{-1}$ and v(C═C) (), at about 1660 $cm^{-1}$, respectively (FIG. 17A). For example, the typical shifts from 700 to 900 $cm^{-1}$ all related to the catechol moiety vibrational modes[41] are present in the monomer and in the crosslinker, but not in the initiator. Conversely, the peak at 1002 $cm^{-1}$, related to the breathing mode of aromatic ring, is present only in the initiator. This peak is considered to be stable and not affected by the cross-linking, therefore it was chosen as an internal control for spectra interpretation (see Methods). Together with these peaks disclosed embodiments also observe the typical peaks related to the C—H deformation at about 1450 $cm^{-1}$ and the peaks at about 1615 $cm^{-1}$ related to v(C—C) of cyclic aminoacids. These peaks are present in all the species. FIGS. 18A-18D illustrate Raman spectra of individual molecules composing the glue and the mixture without initiator before and after curing, with peak assignments monomer (FIG. 18A) crosslinker (FIG. 18B) initiator (LAP only, FIG. 18C), and a mixture of monomer and crosslinker without initiator (FIG. 18D). To be noted the UV curing on the single species (FIGS. 18A-18C) or on the mixture without initiator (FIG. 18**D) has no detectable effect on the Raman spectra. Disclosed embodiments would like to point out how these measurements are not sensitive enough to detect the presence of radical species generated by UV illumination on the sample.

The two major differences between before and after curing Raman spectra are the relative intensities of the peaks at about 960 $cm^{-1}$ and 1660 $cm^{-1}$ (FIG. 17A). Based on the literature disclosed embodiments can assign the shift at 960 $cm^{-1}$ to both v(C—C)[42,43] and a contribution from v(P═O).[44] On the other hand, because disclosed embodiments are in the presence of peptides, the straightforward attribution of the peak at 1660 $cm^{-1}$ goes to the v(C═O) of the Amide I vibration, although this shift can also be assigned to v(C═C). Indeed both the peaks are present in LAP and the monomers and crosslinker alone (FIGS. 18A-

18D), thus evidencing that both possibilities are present.[45] The chemical reaction occurring upon curing of the solution will harden the material by cross-linking. The final effect is a gain of C—C bonds and a reduction of C═C bonds. This effect is directly visible in the increase of the peak at 960 $cm^{-1}$ (v(C—C) (*) in FIG. 13) and decrease of the peak at 1660 $cm^{-1}$ (v(C═C) (**) in FIG. 14). Moreover, the decrease of the 1660 $cm^{-1}$ peak intensity can also be related to the reduced free vibration of the Amide bond, due to the cross-linked structure of the hardened glue. (The bands at 1094 and 838 $cm^{-1}$ are assigned to "v C—N" and "P—N" for the P—N—C group.)

Figure 19A:
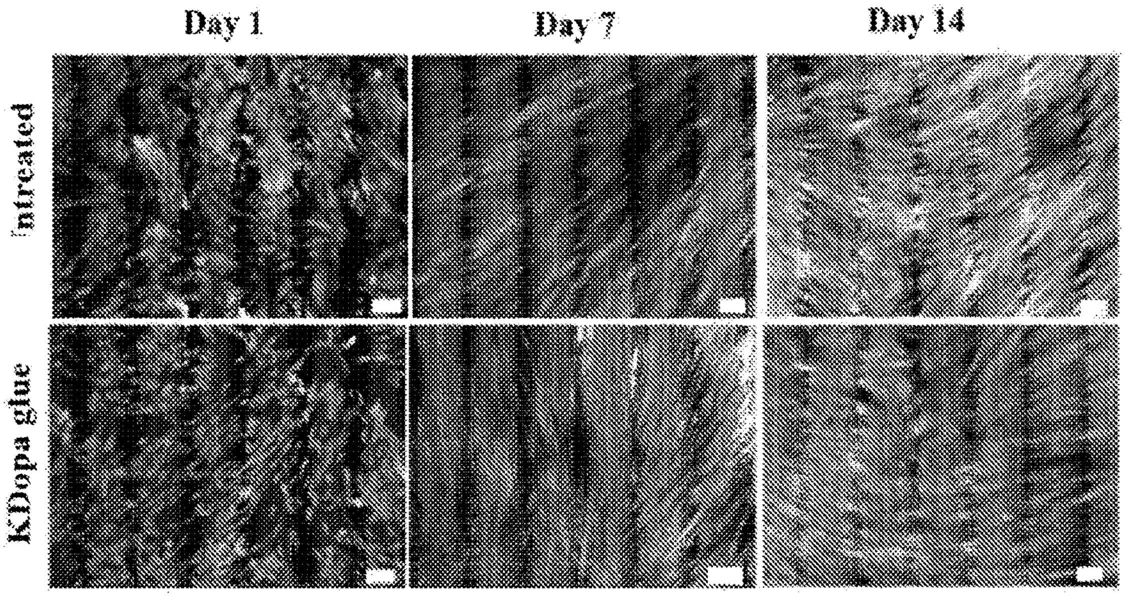
FIGS. 19A-19C illustrate Cytocompatibility and morphology of human dermal fibroblast cells cultured with KDopa glue according to one embodiment of the present disclosure.

After studying the innate properties of the KDopa glue, disclosed embodiments tested the effect of the disclosed glue on cell viability, metabolic activity, and morphology. Human dermal fibroblast cells (HDF) were cultured with the KDopa glue for different time points then, the cytotoxicity of KDopa glue was tested first using live/dead assay. The results are shown in FIG. 19A which exhibited high cell viability with an increase in the cell growth rate during the culture time, thus indicating that there is no cytotoxicity associated with the KDopa glue on the cells. FIG. 19A illustrates Live/dead cells viability assay of cells stained with calcein-AM (green, live cells) and ethidium homodimer-1 (red, dead cells) with scale bar of 100 μm.

Figure 19B:
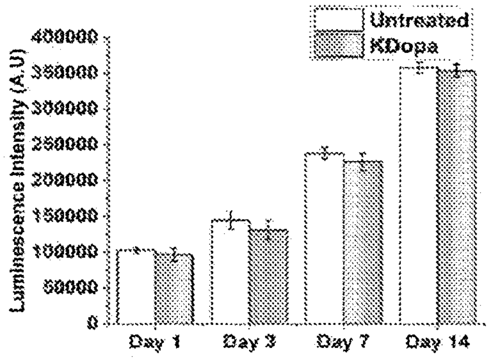
Figure 19C:
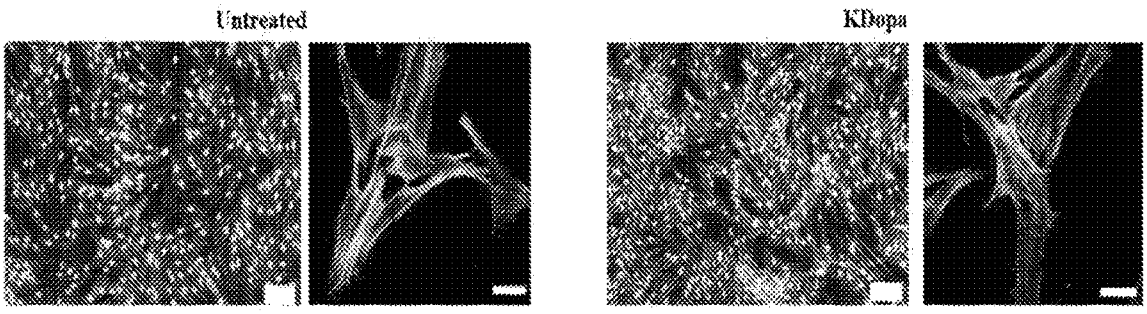

Additionally, the cell proliferation rates were measured. The production of ATP, which indicates the cell's metabolic activity, was found to be increased with culture time with no difference compared to the control (FIG. 19B). FIG. 19B illustrates assessment of cell proliferation for cells cultured with and without KDopa glue for 1, 3, 7, 14 days. Focal adhesions act as force sensors between cells and their surrounding environment through anchored actin microfilament bundles.[46,47] As such, the cells were immunostained with F-actin using phalloidin to label the cytoskeletal arrangement. Highly stretched and elongated cells showed well-defined actin fibers was observed as shown in FIG. 19C similar to the control indicating the normal and healthy morphology of HDF cells. FIG. 19C illustrates immunofluorescence staining of cell nucleus and of cytoskeleton protein F-actin. (F-actin: green, nucleus: blue) after 3 days in culture with scale bar of 100 μm and 20 μm.

Figure 20A:
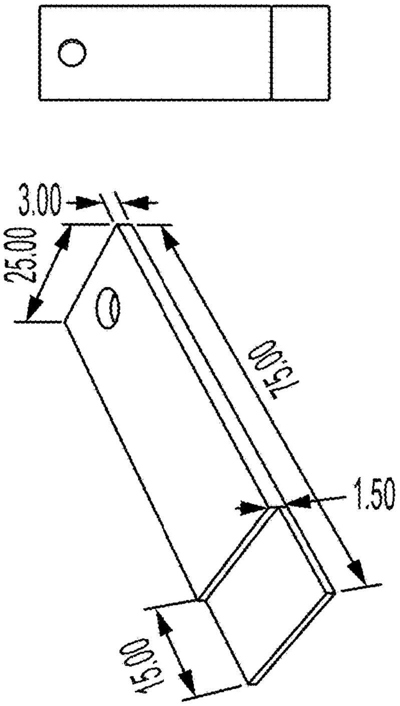
FIG. 20A illustrates dimensions of the polymeric 3D printed specimens according to one embodiment of the present disclosure.
Figure 20B:
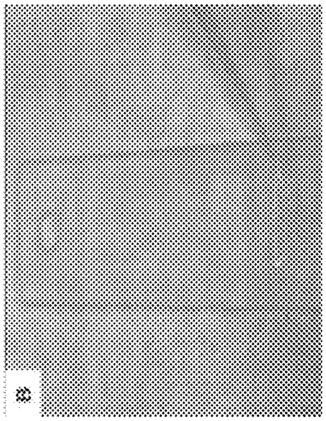
FIG. 20B illustrates KDopa glue added to the strip using a pipette according to one embodiment of the present disclosure.
Figure 20C:
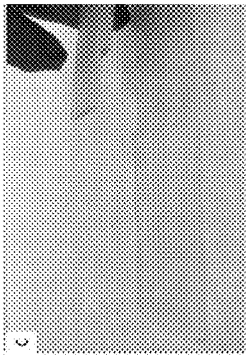
FIG. 20C illustrates two identical strips placed above each other according to one embodiment of the present disclosure.
Figure 20D:
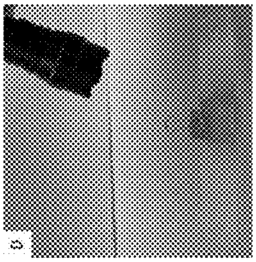
FIG. 20D illustrates the glue is cured using a 400 nm UV flashlight according to one embodiment of the present disclosure.
Figure 20E:
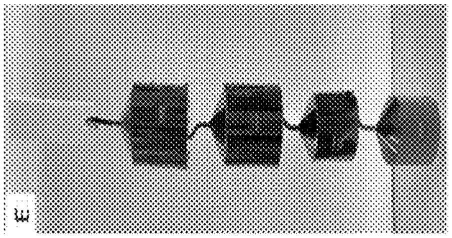
FIGS. 20E-20F illustrate weights lap-shear tests of the glued polymeric specimens according to one embodiment of the present disclosure.
Figure 20F:
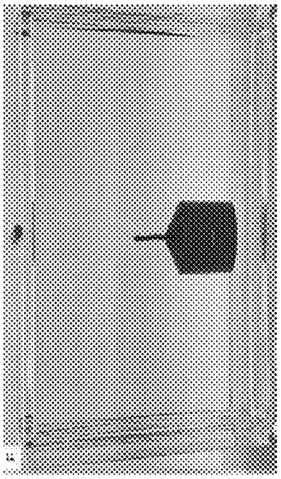

Qualitative experiments were first conducted to evaluate the adhesive properties of the disclosed proposed glue. Specifically, polymeric specimens were 3D printed in specific dimensions by a photocurable resin for manual lap shear test (units in mm) (FIG. 20A). To control the bonded area, a recessed surface has been made with an area of 375 $mm^2$. 20 μl of the KDopa adhesive was applied to glue the two specimens (FIGS. 20B-20D) and weights were introduced as shown in FIGS. 20E-20F. 3 kg weights hooked to the glued strips out of the water (FIG. 20E). 1 kg weight hooked to the glued strips underwater (FIG. 20F). The glue is cured using a 400 nm UV flashlight and photopolymerization of the glue for 30 seconds (FIG. 20D). The glued pieces were able to hold the weights for months, even underwater.

Figure 20G:
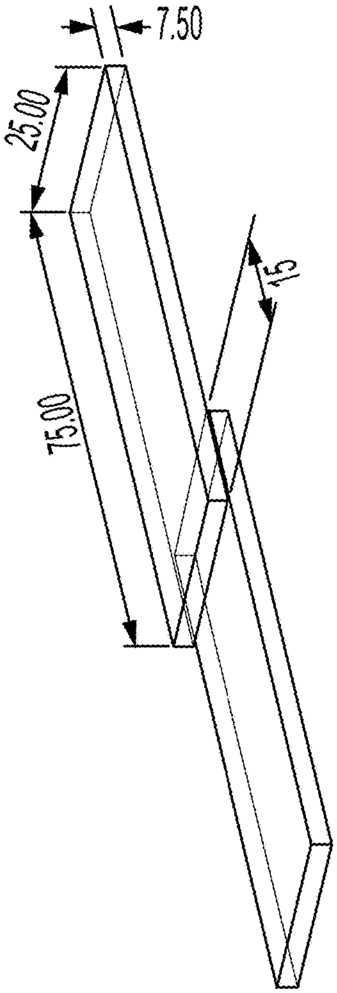
FIG. 20G illustrates dimensions in nm and configuration of the glass slides used for the lap-shear strength test according to one embodiment of the present disclosure.
Figures 21A, 21B, 21C, 21D, 21E:
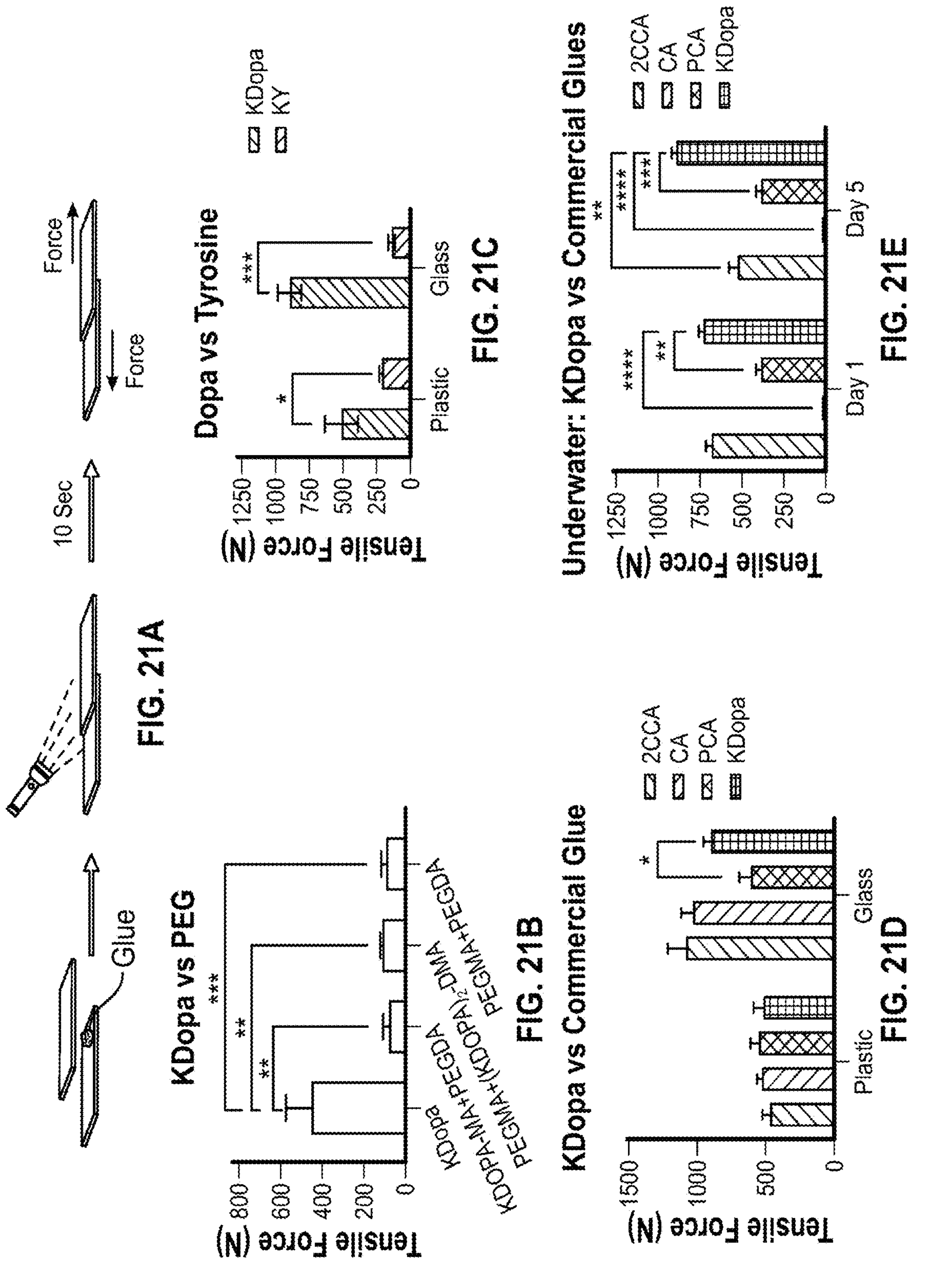
FIG. 21A illustrates schematic illustration of the lap-shear test after applying the KDopa glue according to one embodiment of the present disclosure.
FIG. 21B illustrates comparison of the tensile force between different formulations of monomers and cross-linkers in plastic specimens according to one embodiment of the present disclosure.
FIG. 21C illustrates Dopa versus Tyr glues tensile force comparison in both plastic and glass according to one embodiment of the present disclosure.
FIG. 21D illustrates tensile force comparison of KDopa glue with commercial adhesives on plastic and on glass in dry conditions according to one embodiment of the present disclosure.
FIG. 21E illustrates tensile force comparison of KDopa glue with commercial adhesives on plastic and on glass underwater according to one embodiment of the present disclosure.
Figure 24:
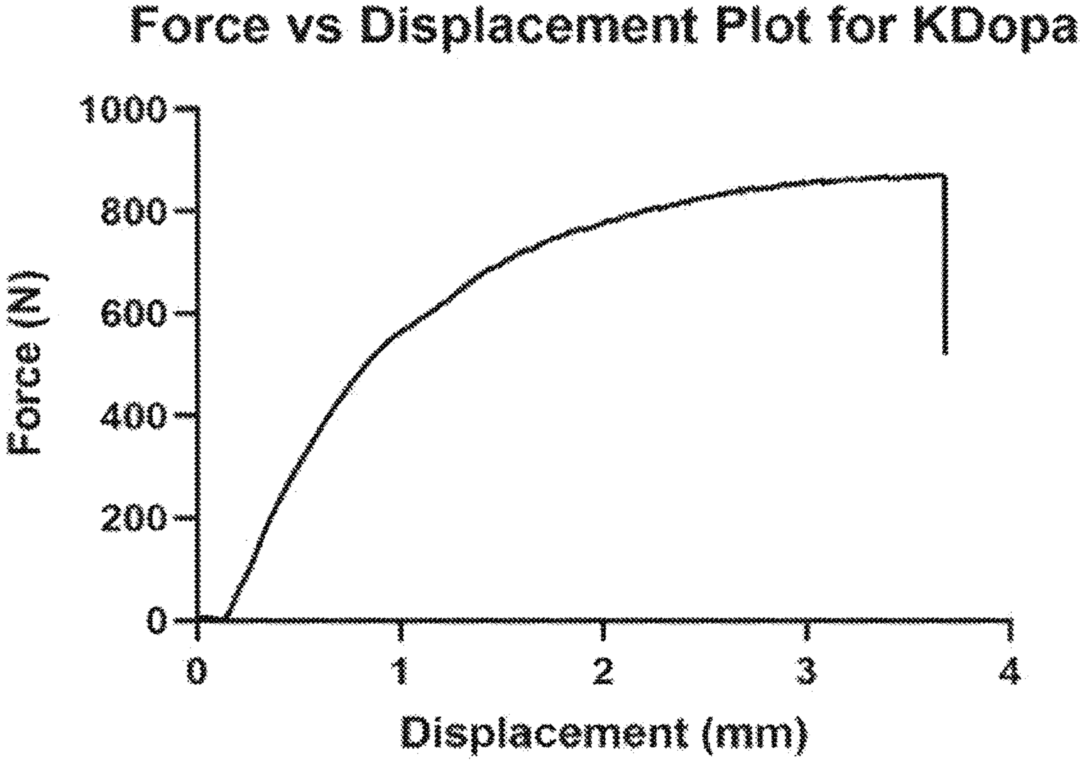
FIG. 24 illustrates a representative force versus displacement plot for The KDopa glue applied to glass according to one embodiment of the present disclosure.

To measure the adhesion strength of the KDopa glue, disclosed embodiments performed a lap-shear strength test where the two adherents were pulled apart in a controlled way by a testing machine, thus enabling the quantification of the bonding strength (FIG. 21A). The adhesive was applied (20 μl) and cured for 10 sec on the same surface area to glue glass slides (FIG. 20G) or polymeric specimens (FIG. 20B). The measurements were recorded as the tensile force versus the displacement plots (FIG. 24). To confirm the importance of monomer and crosslinker to the adhesion properties of KDopa, disclosed embodiments replaced KDOPA-MA or $(KDOPA)_2$-DMA individually with the same molar ratio of PEGMA and PEGDMA respectively, which are also hydrophilic with similar molecular weight. When one of the compounds of KDopa glue was replaced with the PEG analogue, the tensile force was significantly lower. Specifically, for the glass surface, the tensile force was too small to measure and in the case of the plastic, the force was around 80 N, more than five times smaller than that of KDopa glue (FIG. 21B). Disclosed embodiments also replaced the disclosed crosslinker with methylene bis-acrylamide for comparison, but in the same concentration and molar ratio as the disclosed formulation, the solution after the curing was gelly thus, no measurements were recorded (data not shown).

The role of the DOPA amino acid in the adhesive strength was also evaluated by comparing KDOPA-MA with KY-MA, while the crosslinker in both cases remained the $(KDOPA)_2$-DMA. The tensile forces for KDopa were 500 N and 850 N for plastic and glass, respectively, while for the KY adhesive, they were around 200 N in both materials (FIG. 21C). It is well-known than the cation-π interactions between the Lys and DOPA contribute to the adhesive properties. Although these interactions are the same as in the case of Lys and Tyr (cohesive forces), the difference in the tensile forces can be attributed to the hydrogen bond interactions of the catechol group. Indeed the difference in the tensile strength between KDopa and KY is more incisive on the glass surface, where hydrogen bonds are present. Furthermore, disclosed embodiments compared the adhesiveness of KDopa with commercial glues, including a two-component cyanoacrylate adhesive (2CCA), a single-component cyanoacrylate adhesive (CA), and a photocurable adhesive (PCA). FIG. 21D describes tensile force comparison of KDopa glue with commercial adhesives (2CCA: 2 components cyanoacrylate adhesive, CA: cyanoacrylate adhesive, PCA: photocurable adhesive) on plastic and on glass in dry conditions. An equal amount from all the glues (20 l) was applied to the plastic and the glass slides. The measurements on plastic resin showed no significant difference in the adhesive strength for all the glues. On the other hand, cyanoacrylate glues demonstrated around 10% higher tensile force than KDopa glue while the photocurable adhesive showed a significant reduced tensile force than the disclosed glue (FIG. 21D).

The same study was conducted on a glass surface, where all the commercial and Kdopa glues were applied underwater and lap-shear test measurements were recorded one and five days after the application (FIG. 21E). The PCA demonstrated an average tensile force (350 N) constant for both time points. The CA was not able to glue the two glass surfaces since the small applied quantity of the glue was polymerized instantly underwater and became fragile. On the other hand, the 2CCA showed strong tensile force (700 N) underwater even though the performance was slightly decreased after 5 days. The overall performance of the Kdopa glue was superior to the others when applied underwater. After 1 day the tensile force was recorded 750 N and after 5 days was increased to 900 N, probably due to the formation of more hydrogen bonds over time between the glass surface and the catechol group.

The facile synthesis, the eco-friendliness (no use of organic solvents), the no-toxicity, the instant activation with light, the high adhesive strength, and the ease of implementation underwater render the KDopa glue a candidate for various applications. Preliminary experiments with wet tissues (mouse hearts) showed that the glue could potentially be used as a hemostatic agent (e.g., during surgeries).

Figure 22:
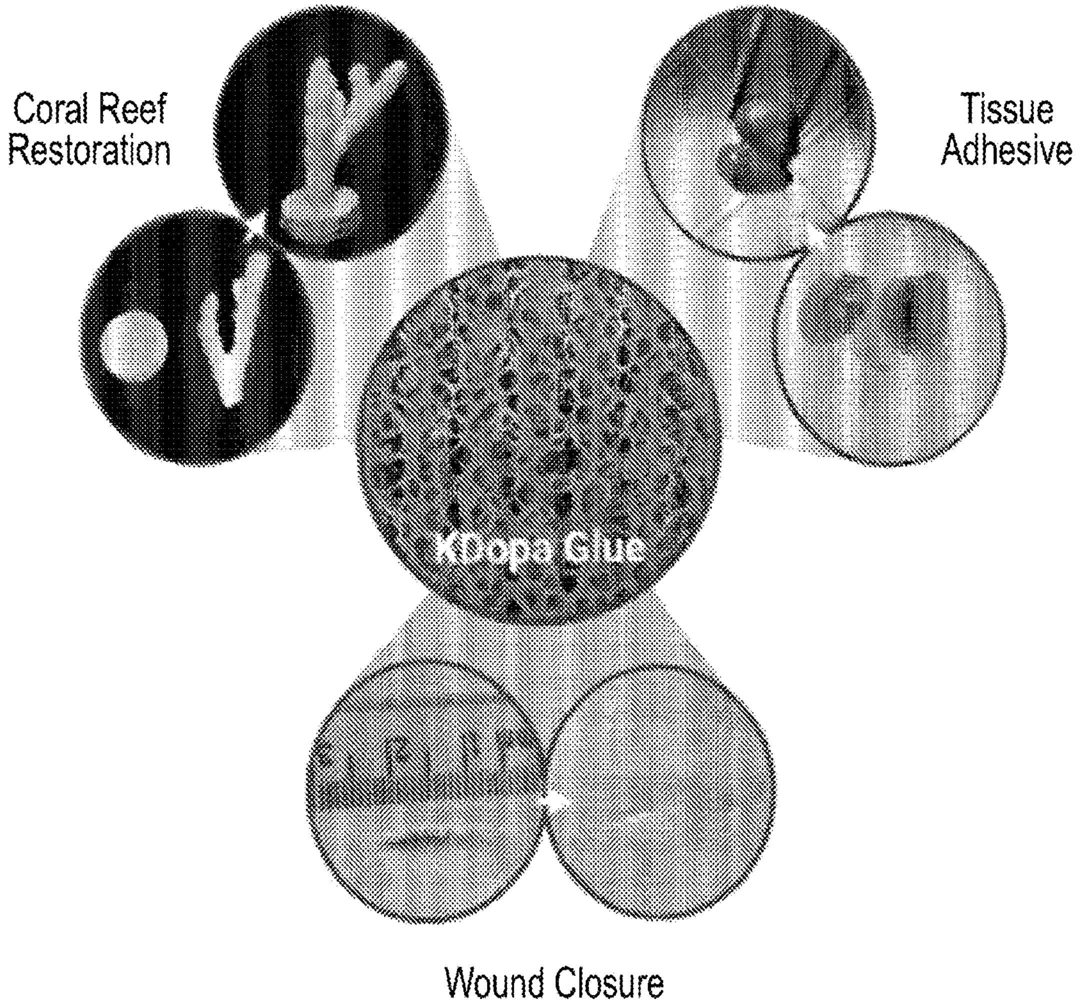
FIG. 22 illustrates various applications of the KDopa glue according to one embodiment of the present disclosure.

Furthermore, the straightforward closing of a 2 cm cut in a mouse's skin almost instantly indicates that the adhesive can find application in wound closure as a replacement for the stitches (FIG. 22).

Figure 23:
FIG. 23 illustrates *Acropora hemprichii* fragments glued on tiles with Kdopa according to one embodiment of the present disclosure.

A non-toxic, easy-to-apply adhesive is valuable for environmental application too. Specifically, the disclosed adhesive was used to glue coral fragments according to the microfragmentation approach.[37] Small coral fragments are placed on tiles in an aquarium tank under controlled conditions (coral nurseries) and let grow to a specific size until they are positioned back in the sea. After monitoring the fragments that were glued with the Kdopa for 3 months, disclosed embodiments observed no sign of toxicity or detachment (FIG. 23). With a great increase in demand for coral restoration around the globe by using more eco-friendly and sustainable materials, Kdopa glue can be effectively applied in microfragmentation as a replacement for the traditionally used cyanoacrylate adhesives. Disclosed embodiments are currently studying the growth of coral fragments from different species in a controlled environment and in the field, and the disclosed findings will be presented in a forthcoming paper.

CONCLUSION

Benefiting from the well-studied synergy of Lys and DOPA to adhesion, especially underwater, disclosed embodiments rationally designed and synthesized a monomer and a crosslinker to serve as the adhesive's components. An aqueous solution of these two compounds and a biocompatible initiator can instantly form a solid polymeric network upon exposure to UV light, consisting exclusively of these two amino acids and a photoinitiator. The simple synthetic procedure, mainly for the crosslinker, can open new avenues for synthesizing more complicated molecules like a multiple-armed crosslinking agent if the coupling of the bifurcation molecule is achieved more than once. Copolymerization of the two compounds with other monomers can lead to a very interesting and ambitious category of materials like stimuli-responsive glues. Lap-shear tests confirmed both compounds' importance to the glue's adhesive strength, while the DOPA amino acid proved the enhanced adhesiveness over the tyrosine. Comparing the disclosed glue with commercial ones demonstrated similar values of tensile forces, proving its efficiency. To conclude, the disclosed proposed glue can find applications from the biomedical field to rising environmental challenges like coral reef degradation.

Figure 25:
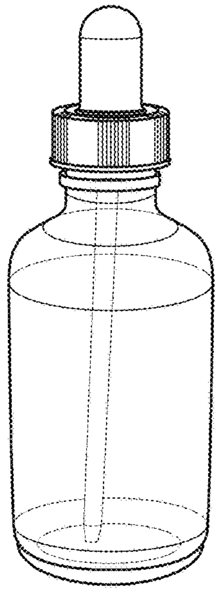
FIG. 25 illustrates a dropper/closure device for delivering a peptide-based adhesive material according to one embodiment of the present disclosure according to one embodiment of the present disclosure.
Figure 26:
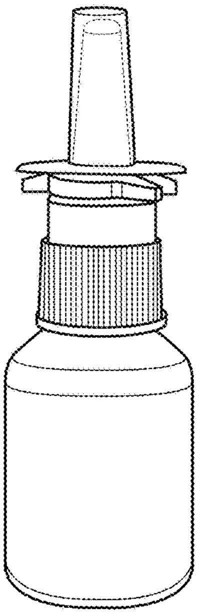
FIG. 26 illustrates a squeeze bottle pump spray device for delivering a peptide-based adhesive material according to one embodiment of the present disclosure according to one embodiment of the present disclosure.
Figure 27:
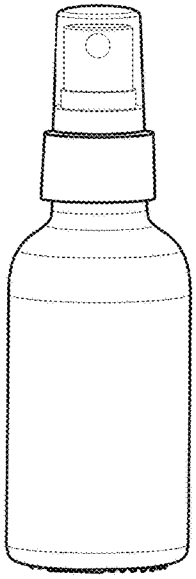
FIG. 27 illustrates an airless and preservative-free spray device for delivering a peptide-based adhesive material according to one embodiment of the present disclosure according to one embodiment of the present disclosure.
Figure 28:
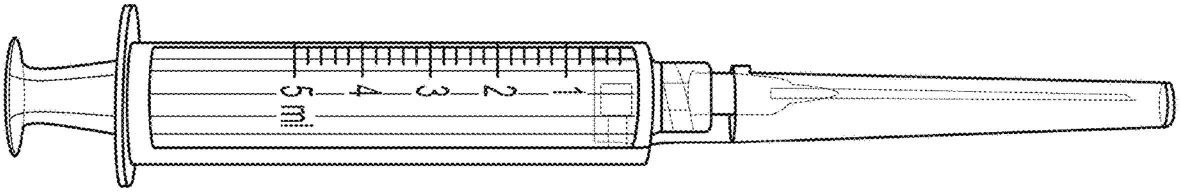
FIG. 28 illustrates an injectable device for delivering a peptide-based adhesive material according to one embodiment of the present disclosure according to one embodiment of the present disclosure.

While preferred methods and devices of the present disclosure may include the device selected from the group consisting of a container with a dropper/closure device (FIG. 25), a squeeze bottle pump spray (FIG. 26), an airless and preservative-free spray (FIG. 27), and an injectable device (FIG. 28), it is readily appreciated that skilled artisans may employ other means and techniques for delivering the peptide-based adhesive material.

The injectable device (FIG. 28) may not be limited to syringe-type device. One of ordinary skill in the art would readily appreciate that any injectable device suitable for delivering the peptide-based adhesive material may be utilized according to aspects of the present disclosure.

One of ordinary skill in the art would readily appreciate that any kind of device suitable for delivering the disclosed products described in the present disclosure may be utilized.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Materials and Methods

Materials

MBHA Rink Amide resin, Fmoc-Lys(Boc)-OH, Fmoc-Lys(Fmoc)-OH, Fmoc-Dopa(Acetonide)-OH, Fmoc-Tyr (tBu)-OH, (2-(1H-benzotriazol-1-yl)-1,1,3,3-tetramethyluronium hexafluorophosphate (TBTU)), and hydroxy benzotriazole (HOBt) were purchased from GL Biochem, China. Lithium phenyl-2,4,6-trimethylbenzoylphosphinate (LAP), Poly(ethylene glycol) methacrylate (PEGMA, $M_n$=360), Poly(ethylene glycol) diacrylate (PEGDA, $M_n$=700), piperidine, trifluoroacetic acid (TFA), methacrylic anhydride, triisopropylsilane (TIS), N,N-dimethylformamide (DMF), N,N-Diisopropylethylamine (DIPEA), dichloromethane (DCM) and diethyl ether were purchased from (Sigma-Aldrich Chemical Co.). All chemicals were used as received, without purification. The photopolymer resin that was used for the plastic specimens was bought from Formlab.

Synthesis

Synthesis of the KDOPA-MA

The synthesis of the KDOPA-MA monomer was performed in two steps. In the first step, the KDOPA dipeptide was synthesized by Solid Phase Peptide Synthesis (SPPS) using a CS136X CS Biopeptide synthesizer. The peptide coupling was conducted on rink amide resin by aging the resin in a mixture of TBTU (3eq.), HOBt (3eq.) DIPEA (6 eq.), and Fmoc-protected amino acid (3eq.). Disclosed embodiments used 20% (v/v) piperidine/DMF to deprotect the Fmoc group on the N-terminus of the peptide sequence before continuing to the next coupling step. After coupling the last amino acid to the peptide sequence the resin was then transferred out of the synthesizer. In the second step, the N-terminus of the dipeptide was deprotected with the piperidine mixture, the resin washed thoroughly and placed in a round bottom flask with 50 mL of DMF and methacrylic anhydride (10 fold excess to the resin loading capacity). The solution left to react for 2 h at 60° C. and then at room temperature overnight. After the completion of the reaction, the resin washed with DMF and DCM and the peptide was then cleaved from the resin using a mixture of 95% v/v TFA, 2.5% v/v water and 2.5% v/v TIS for 2 h at room temperature. The filtrate was collected in a flask and the peptide was precipitated after the addition of cold diethyl ether. The solution was centrifuged at 4000 rpm for 5 min at 10° C. and the solid was dried under vacuum overnight. A reverse phase-HPLC purification system using a C-18 column was used for the peptide purification. $^1$H NMR (400 MHz, DMSO) δ 8.67 (d, J=5.5 Hz, 2H), 7.80 (dd, J=63.2, 7.9 Hz, 2H), 7.20 (dd, J=120.7, 2.1 Hz, 2H), 6.69-6.34 (m, 3H), 5.71 (d, J=1.5 Hz, 1H), 5.39 (t, J=1.5 Hz, 1H), 4.32 (td, J=8.3, 5.2 Hz, 1H), 4.21 (td, J=8.3, 5.6 Hz, 1H), 2.88-2.57 (m, 4H), 1.86 (t, J=1.1 Hz, 3H), 1.69-1.41 (m, 4H), 1.23 (qt, J=14.8, 7.1 Hz, 2H).

Synthesis of the KY-MA

The synthetic procedure for the KY-MA monomer was the same as described above by only replacing DOPA with Tyr. $^1$H NMR (400 MHz, DMSO) δ 9.18 (s, 1H), 7.81 (dd, J=61.2, 8.0 Hz, 2H), 7.46-7.04 (m, 2H), 7.02-6.56 (m, 4H), 5.71 (s, 1H), 5.40 (t, J=1.6 Hz, 1H), 4.34 (td, J=8.4, 5.0 Hz, 1H), 4.22 (td, J=8.5, 5.6 Hz, 1H), 2.95-2.63 (m, 4H), 1.87 (t, J=1.1 Hz, 3H), 1.72-1.39 (m, 4H), 1.23 (tq, J=13.9, 7.2 Hz, 2H).

Synthesis of the $(KDOPA)_2$-DMA

The difference in the synthesis of the $(KDOPA)_2$-DM was that the first amino acid attached to the resin was the Fmoc-Lys(Fmoc)-OH. After the deprotection of the Fmoc group the loading capacity of the resin is doubled and the stoichiometry should adjust accordingly. $^1$H NMR (400 MHz, DMSO) δ 8.85-8.50 (m, 4H), 8.05-7.71 (m, 6H), 7.11 (d, J=53.0 Hz, 2H), 6.73-6.33 (m, 6H), 5.71 (d, J=4.7 Hz, 2H), 5.40 (dd, J=4.3, 2.5 Hz, 2H), 4.46-4.27 (m, 2H), 4.25-4.04 (m, 3H), 3.10-2.57 (m, 10H), 1.86 (d, J=4.5 Hz, 6H), 1.73-1.03 (m, 17H).

Synthesis of Adhesives

The adhesive was prepared using the formulation of Table 1. An aqueous solution of LAP photoinitiator (15 mg/ml), KDOPA-MA (350 mg/ml) and (KDOPA)2-DMA (145 mg/ml) was prepared by mixing and vortexing for 10 sec. Throughout the text this formulation mentioned KDopa glue. When KDOPA-MA was replaced with KY-MA (the (KDOPA)2-DMA crosslinker remains the same) disclosed embodiments have the KY glue. The solution was applied to different surfaces and after the exposure to a 395 nm wavelength light, the polymerization initiated and the solution solidified to glue the substrates.

TABLE 1

Concentrations of the compounds for the KDopa glue in 1 ml of water. Formulation

| Compound | Molecular Weight | Amount | Molarity |
|---|---|---|---|
| $(KDOPA)_2$-DMA | 896 (g/mol) | 145 mg | 161.8 mM |
| KDOPA-MA | 392 (g/mol) | 350 mg | 892.8 mM |
| LAP | 294.21 (g/mol) | 15 mg | 50.9 mM |
| MiliQ Water | | 1 mL | |

Methods

Nuclear Magnetic Resonance (NMR)

The NMR spectra ($^1$H and $^{13}$C) of purified peptides were recorded using a Bruker Avance III 400 MHz NMR spectrometer equipped with a cryoprobe. The samples were prepared by dissolving 5 mg peptide powder in 700 μl of d6-DMSO (Cambridge Isotope Laboratories, U.S.A.). Bruker Topspin 3.5pl7 software (Bruker BioSpin, Rheinstetten, Germany) was used for data collection, while data analysis was conducted on MestReNova (Mestrelab Research, Spain). For the Solid-State NMR, the $^{13}$C Magic Angle Spinning (MAS) NMR spectra were recorded using W. B. Bruker 400 AVANAC III spectrometer equipped with 4 mm double resonance CP MAS Bruker Probe (Bruker-BioSpin, Rheinstetten, Germany). Cp pulse program from Bruker pulse library was choosen with a recycling delay time of 5 s and 14 kHz spinning rate. The samples were lyophilized. Bruker Topspin 3.5pl7 software and MestReNova were used for both data collection and analysis.

Raman Spectroscopy

Raman spectroscopy measurements were performed with Witec Alpha 300 RA confocal Raman spectroscope, with linearly polarized 532 nm wavelength excitation laser, with a grating resolution of 300 g/mm. Spectra were acquired in confocal configuration through a 50× objective (Zeiss LD EC Epiplan-Neofluar). For each sample, spectra with integration time of 5s and 5 accumulations were acquired. Measurements were performed before and after curing. Specifically, a 400 nm wavelength flashlight was applied for 30 seconds to each sample. Data analysis was performed by using Origin Pro 8 software. For the simple peak assignment, peak finder routine with constant baseline subtraction and detection of maximum peak height with a threshold of 7, was used on single spectra. For the comparison of the area under the peaks that are estimated to be changing after cross-linking, disclosed embodiments performed the following. Three spectra were collected for the mixture before and after curing. Subsequently, each spectrum was baseline subtracted with a polynomial of $5^{th}$ order. The count's values were normalized to the peak at 1002 $cm^{-1}$, belonging to the aromatic ring of the initiator (LAP). Afterward, the three spectra were averaged. From the two peaks identified at about 966 $cm^{-1}$ and 1660 $cm^{-1}$, a Gaussian curve was fitted to the peak, and the change in area under the curve before and after the curing was recorded. Spectra are all plotted with an offset.

Liquid Chromatography-Mass Spectroscopy (LC-MS)

1 mg/ml of every compound solution in water were analyzed by an Agilent 1260 Infinity LC equipped with Agilent 6130 Quadrupole MS. Agilent Zorbax SB-C18 4.6×250 mm column was used together with a mixture of two different solutions of 0.1% (v/v) formic acid—water (A) and 0.1% (v/v) formic acid—acetonitrile (B). The flow of the mobile phase was 1.5 ml/min, with a composition of 98% A-2% B in the first 30 seconds. From 0.5 to 11.5 mins, the flow of B increased to 98% B and turned back again to 2%. LC chromatogram was obtained at a wavelength of 220 nm.

Scanning Electron Microscopy (SEM)

The samples were lyophilized, mounted on carbon tape, and sputter-coated with 5 nm Ir before imaging. SEM images were taken using a Teneo VS Scanning Electron Microscope with an accelerating voltage of 5 kV.

Adhesion Property Test (Lap Shear Strength Test)

Adhesion properties were determined by lap shear strength tests. 20 μL of different adhesives was applied to polymeric and glass specimens and cured by a UV-VIS flash light. To explore the underwater adhesion strength of the glues, a glass slide was submerged into a tank of water. Then 40 μL of the glue was deposited onto one slide underwater and the second piece of the glass was then placed on top of the first specimen to create a lap shear join and cured with UV light (when needed) to initiate the crosslinking of the glue. The assembled slides was tested and were recorded over two time points (Day 1 and Day 5). At Day 1 and 5, the slide was removed from the tank and pulled apart immediately and tensile force was recorded. The static tensile tests of bulk adhesive were performed using an Instron universal testing machine model "5565A" with "5 kn" loadcell connected to the moving crosshead, the machine has electromechanical drive system). The test rate used is 4 mm/min, all tests are done in room temperature. The gripping is performed using "5Kn double sided screw grips", the lower grip is installed to the fixed crosshead, while the upper grip is fixed on a bearing in the moving crosshead to minimize the shear effect on the sample. The maximum load (force) was divided by the overlapping contact area of the specimens to calculate adhesion strength. Tests were performed at least the disclosed times for each type of adhesive, and data points were averaged.

Statistical Analysis

The results are represented as mean±standard deviation, n≥3. The differences between different groups were analyzed using a student's t-test, and values with $p<0.05$ were considered statistically significant.

In Vitro Evaluation

Cytocompatibility

For the cytocompatibility studies, small disks were prepared using freshly prepared KDopa glue. Briefly, a drop of 1 μL was placed into a small petri dish to form a uniformed disk, and then the disks were cured using a 400 nm UV flashlight for 5 minutes to ensure efficient crosslinking. Then, the disks were washed 3× using MiliQ water to remove excess monomer units and then incubated in full DMEM media for 4 the disclosed s, followed by double washing with MiliQ water and 1×PBS three times to remove DMEM. The prepared glue disks were then placed under UV for 30 minutes to sterilize them before culturing them with the cells.

Cell Culture

Human dermal fibroblast cells (HDF) were cultured with DMEM/high-glucose media supplemented with Glutamax, 10% FBS, and 1% Penicillin/streptomycin (GIBCO, ThermoFisher, USA). To maintain the cells were they were cultured in a T75 cell culture flask and placed in a humidified incubator at 37° C. with 5% C02 and 95% air. Once the the cells reached approximately 80% of confluency they were subcultured by trypsin, while maintaining fresh media by changing it every 2-3 days.

Live/Dead Staining

To assess the toxicity of the synthesized material to the cultured cells, a Live/Dead Viability/Cytotoxicity Kit (ThermoFisher, USA) were used. First, $10\times10^3$ of cells were seeded in each well of 96 wells plate. A disk of KDopa glue was placed in each well before seeding the cells. After the seeding, the plate were incubated in a CO2 incubator at 37° C. and 5% CO2. Then, a mixture of calcein acetoxymethyl ester (Calcein-AM) and ethidium homodimer-I (EthD-I) dyes were used to detect viable cells and dead cells respectively. Briefly, The media were removed from cells in the wells, then they were washed with dulbecco's phosphate-buffered saline (D-PBS). Then, the final staining solution was prepared by mixing 100 μL of the initial staining compound with Calcein-AM and EthD-1 in 1×PBS at ratio 1:2 (Molar ratio) and then was added to each well and incubated at room temperature for 30 minutes. The staining solution was removed after incubation, and DPBS was added to the wells for imaging. The cells were imaged under an inverted microscope (Zeiss Axio Observer Z1 microscope, Carl Zeiss, Oberkochen, Germany). The viability of the cells was assessed at three time points (Day 1, Day 3, and Day 7).

CellTiter-Glo® Luminescent Viability Assay

Cell proliferation and metabolic activity of cells cultured with a KDopa glue were assessed using CellTiter-Glo® 3D Cell Viability Assay (Promega, Germany). This assay relies on ATP quantification technique by detecting luminous signal produced by metabolically active cells in the presence of thermostable luciferase. Manufacturer's recommended protocol was followed, where CellTiter-Glo® 3D reagent equivalent to the amount of the media in the wells was added. Then, each well was vigorously mixed after the addition of the reagent, and incubated at room temperature for 30 minutes. The luminous signals were measured using a plate reader (PHERAstar FS, Germany). The metabolic activity of the cells was assessed at three time points (Day 1, Day 3, and Day 7).

Immunostaining

To study the morphology of cells cultured with and without KDopa glue, the Actin cytoskeleton was observed at a different time point of culture.[39] A 4% paraformaldehyde solution was used for 30 minutes for cell fixation. Then, to permeabilize the membrane of the cells a cold cytoskeleton buffer (3 mM $MgCl_2$, 300 mM sucrose and 0.5% Triton X-100 in PBS solution) was used for 5 minutes followed by incubation of the cells in blocking buffer (5% FBS, 0.1% Tween-20, and 0.02% sodium azide in PBS) for 30 minutes. Lastly, to immunostain the cytoskeleton, F-Actin, rhodamine-phalloidin (1:300) was used and incubated with cells for 1 the disclosed. Then, the nucleus was stained by using DAPI (1:2000) in water for five minutes. The immunostained cells were then imaged using a laser-scanning confocal microscope (Leica Stellaris Confocal Microscope, Germany).

Applications

The Kdopa glue was used in various applications. First, two freshly extracted hearts from mice were glued by applying 20 μL of the Kdopa adhesive. The two hearts were hold in place during the curing process (395 nm UV light for 20 sec). Second, mouse skin was used as a model to evaluate possible wound closure applications. A 2 cm incision was made in the skin through the subcutaneous tissue of the extracted mouse skin. Then, the cut was closed by applying 20 μL of the KDopa glue and cured for 20 sec using a 395 nm UV flashlight. Third, the Kdopa adhesive was applied to the coral microfragmentation technique towards coral restoration. The coral used in this study was an *Acropora hemprichii* from the Red Sea. Nine fragments (1-2 cm) were cut from the same donor colony and glued to white cement circular tiles. For each fragment 75 μL of Kdopa glue was used and cured for 20 sec. The coral fragments were placed in shallow water in an indoor polycarbonate tank, the temperature was maintained at 22-25° C. with a constant flow of seawater drawn from deep seawater well from the adjacent reef.

REFERENCES

The following references are referred to above and are incorporated herein by reference:

1. Waite, J. H., "The Formation of Mussel Byssus: Anatomy of a Natural Manufacturing Process," Structure, Cellular Synthesis and Assembly of Biopolymers, 27-54 (1992).
2. Coyne, K. J., et al. "Extensible Collagen in Mussel Byssus: A Natural Block Copolymer," *Science* 277, 1830-1832 (1997).
3. Cui, C., et al. "Recent advances in wet adhesives: Adhesion mechanism, design principle and applications." *Prog. Polym. Sci.* 116, 101388 (2021).
4. Strausberg R. L., et al. "Protein-based medical adhesives." *Trends in biotechnology* 8, 53-57 (1990).
5. Rosano, G. L., et al. "Recombinant protein expression in *Escherichia coli*: advances and challenges." *Front. Microbiol.* 5, 172 (2014).
6. Silverman, H. G., et al. "Understanding Marine Mussel Adhesion." *Mar. Biotechnol.* 9, 2661-681 (2007).
7. Forooshani P. K., et al. "Recent Approaches in Designing Bioadhesive Materials Inspired by Mussel Adhesive Protein." *J. Polym. Sci., Part A: Polym. Chem.* 55, 9-33 (2017).

8. Li, Y., et al. "Single Molecule Evidence for the Adaptive Binding of DOPA to Different Wet Surfaces." *Langmuir* 30, 4358-4366 (2014).
9. Shin, J., et al. "Tissue Adhesive Catechol-Modified Hyaluronic Acid Hydrogel for Effective, Minimally Invasive Cell Therapy." *Adv. Funct. Mater.* 25, 3814-3824 (2015).
10. Yan, S., et al. "Preparation of mussel-inspired injectable hydrogels based on dual-functionalized alginate with improved adhesive, self-healing, and mechanical properties." *J. Mater. Chem. B.* 6, 6377-6390 (2018).
11. Ju, Y., et al. "Engineered Metal-Phenolic Capsules Show Tunable Targeted Delivery to Cancer Cells." *Biomacromolecules* 17, 2268-2276 (2012).
12. Kim, K., et al. "Bio-inspired catechol conjugation converts water-insoluble chitosan into a highly water-soluble, adhesive chitosan derivative for hydrogels and LbL assembly." *Biomater. Sci.* 1, 783-790 (2013).
13. Neto, A. I., et al. "Nanostructured Polymeric Coatings Based on Chitosan and Dopamine-Modified Hyaluronic Acid for Biomedical Applications." *Small* 10, 2459-2469 (2014).
14. Zhou, D., et al. "Dopamine-Modified Hyaluronic Acid Hydrogel Adhesives with Fast-Forming and High Tissue Adhesion." *ACS Appl. Mater. Interfaces* 12, 18225-18234 (2020).
15. Zhu, W., et al. "A novel DOPA-albumin-based tissue adhesive for internal medical applications." *Biomaterials* 147, 99-115 (2017).
16. Gowda, A H J., et al. "Design of tunable gelatin-dopamine based bioadhesives." *Int. J. Biol. Macromol.* 164, 1384-1391 (2020).
17. Di, X., et al. "Bioinspired tough, conductive hydrogels with thermally reversible adhesiveness based on nanoclay confined NIPAM polymerization and a dopamine modified polypeptide." *Mater. Chem. Front.* 4, 189-196 (2020).
18. Tatehata, H., et al. "Model polypeptide of mussel adhesive protein. I. Synthesis and adhesive studies of sequential polypeptides (X-Tyr-Lys)n and (Y-Lys)n." *Jthe disclosed nal of Applied Polymer Science* 76, 929-937 (2000).
19. Ahn, B. K., et al. "High-performance mussel-inspired adhesives of reduced complexity." *Nat. Commun.* 6, 8663-8669 (2015).
20. North, M. A., et al. "High Strength Underwater Bonding with Polymer Mimics of Mussel Adhesive Proteins." *ACS Appl. Mater. Interfaces* 9, 7866-7872 (2017).
21. Zhao, Q., et al. "Underwater contact adhesion and microarchitecture in polyelectrolyte complexes actuated by solvent exchange." *Nat. Mater.* 15, 407-412 (2016).
22. Burke, S. A., et al. "Thermal gelation and tissue adhesion of biomimetic hydrogels." *Biomedical Materials* 2, 203-210 (2007).
23. Montazerian, H., et al. "Stretchable and Bioadhesive Gelatin Methacryloyl-Based Hydrogels Enabled by in Situ Dopamine Polymerization." *ACS Appl. Mater. Interfaces* 13, 40290-40301 (2021).
24. Skelton, S., et al. "Biomimetic adhesive containing nanocomposite hydrogel with enhanced materials properties." *Soft Matter* 9, 3825-3833 (2013).
25. Patil, N., et al. "Mussel-inspired protein-repelling ambivalent block copolymers: controlled synthesis and characterization." *Polym. Chem.* 6, 2919-2933 (2015).
26. Wilker, J. J., "Positive charges and underwater adhesion." *Science* 349, 582-583 (2015).
27. Maier, G. P., et al. "Adaptive synergy between catechol and Lysine promotes wet adhesion by surface salt displacement." *Science* 349, 628-632 (2015).
28. Statz, A. R., et al. "New Peptidomimetic Polymers for Antifouling Surfaces." *J. Am. Chem. Soc.* 127, 7972-7973 (2005).
29. Shin, M., et al. "The position of Lysine controls the catechol-mediated surface adhesion and cohesion in underwater mussel adhesion." *J. Colloid Interface Sci.* 563, 168-176 (2020).
30. Zhang, C., et al. "Tough and alkaline-resistant mussel-inspired wet adhesion with surface salt displacement via polydopamine/amine synergy." *Langmuir* 35, 5257-5263 (2019).
31. Zhang, J., et al. "Quantifying cation-π interactions in marine adhesive proteins using single-molecule force spectroscopy." *Supramolecular Materials* 1, 100005 (2022).
32. Geng, H., et al. "Principles of Cation-π Interactions for Engineering Mussel-Inspired Functional Materials." *Acc. Chem. Res.* 55, 1171-1182 (2022).
33. Tiu, B. D. B., et al. "Cooperativity of Catechols and Amines in High-Performance Dry/Wet Adhesives." *Angewandte Chemie* 132, 16759-16767 (2020).
34. Rapp, M. V., et al. "Defining the Catechol-Cation Synergy for Enhanced Wet Adhesion to Mineral Surfaces. *J. Am. Chem. Soc.* 138, 9013-9016 (2016).
35. Thumwanit, V., et al. "Cytotoxicity of polymerized commercial cyanoacrylate adhesive on cultured human oral fibroblasts." *Aust. Dent. J.* 44, 248-252 (1999).
36. Leggat, P. A., et al. "Surgical applications of cyanoacrylate adhesives: a review of toxicity." *ANZ J. Surg.* 77, 209-213 (2007).
37. Forsman, Z. H., et al. "Growing coral larger and faster: micro-colony-fusion as a strategy for accelerating coral cover." *Peer J.* 3, e1313 (2015).
38. Albalawi, H. I., et al. "Sustainable and Eco-Friendly Coral Restoration through 3D Printing and Fabrication." *ACS Sustainable Chem. Eng.* 9, 12634-12645 (2021).
39. Alshehri, S., et al. "Scaffolds from Self-Assembling Tetrapeptides Support 3D Spreading, Osteogenic Differentiation, and Angiogenesis of Mesenchymal Stem Cells. *Biomacromolecules* 22, 2094-2106 (2021).
40. Greaves, S. J., et al. "Vibrational spectra of catechol, catechol-d2 and -d6 and the catecholate monoanion." *Spectrochim. Acta Part A Mol. Spectrosc.* 47, 133-140 (1991).
41. Maiti, N. C., et al. "Raman Spectroscopic Characterization of Secondary Structure in Natively Unfolded Proteins: α-Synuclein." *J. Am. Chem. Soc.* 126, 2399-2408 (2004).
42. Lima Jr, J. A., et al. "Raman scattering of L-valine crystals." *J. Raman Spectrosc.* 36, 1076-1081 (2005).
43. Nyquist, R. A., "Interpreting Infrared, Raman, and Nuclear Magnetic Resonance Spectra." *Academic Press* 231-350 (2001).
44. Lee, J. Y., et al. "Raman intensities of C=C stretching vibrational frequencies of polyenes: Nodal mode analysis." *J. Chem. Phys.* 107, 4112-4117 (1997).
45. McBeath, R., et al. "Cell shape, cytoskeletal tension, and RhoA regulate stem cell lineage commitment." *Dev. Cell.* 6, 483-495 (2004).

46. Katz, B. Z., et al. "Physical state of the extracellular matrix regulates the structure and molecular composition of cell-matrix adhesions." *Mol. Biol. Cell.* 11, 1047-1060 (2000).

47. Shin, M., et al. "Two faces of amine-catechol pair synergy in underwater cation-π interactions." *Chemistry of Materials* 33, 3196-3206 (2021).

48. Lim, C., et al. "Nanomechanics of poly (catecholamine) coatings in aqueous solutions." *Angewandte Chemie International Edition* 55, 3342-3346 (2016).

49. Miclotte, M. P. J., et al. "Thermoresponsive Block Copolymer Core-Shell Nanoparticles with Tunable Flow Behavior in Porous Media." *ACS Appl. Mater. Interfaces* 14, 54182-5419 (2022).

All documents, patents, the disclosed nal articles and other materials cited in the present application are incorporated herein by reference.

While the present disclosure has been disclosed with references to certain embodiments, numerous modification, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A compound comprising:

a structure of Formula 1,

Formula 1

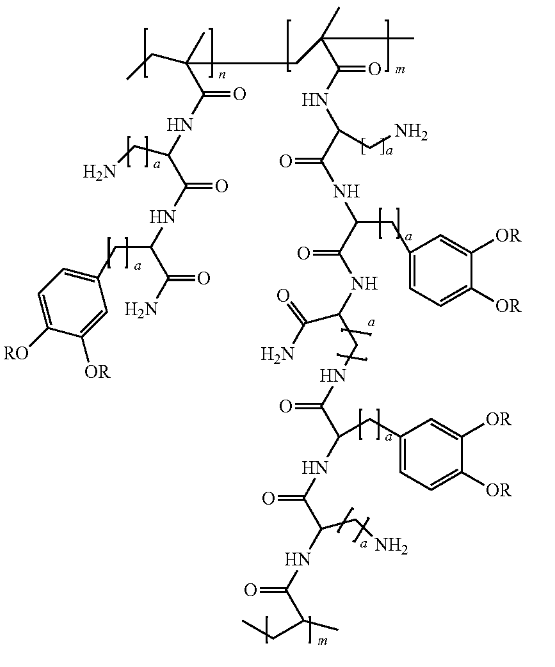

wherein a is from 1 to 6, wherein R is at least one selected from the group consisting of hydrogen, —O—$(CH_2)_b$, and $(CH_2)_b$, and wherein b is from 1 to 6, and wherein n is 3 to 8 times higher than m.

2. The compound of claim 1, wherein the compound is a water-based photoreactive adhesive material and wherein the compound is applied to a substrate under wet or dry condition.

3. The compound of claim 2, wherein the wet condition is salt water or water.

4. A compound comprising:

a structure of Formula 2,

Formula 2

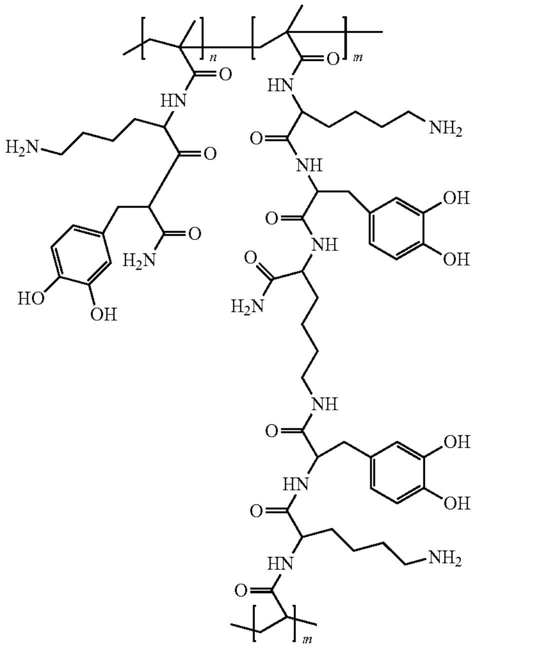

wherein n is 3 to 8 times higher than m.

5. The compound of claim 4, wherein n is 4 to 6 times higher than m.

* * * * *